US007572439B2

(12) United States Patent
Kokai-Kun et al.

(10) Patent No.: US 7,572,439 B2
(45) Date of Patent: Aug. 11, 2009

(54) ENZYME DISRUPTION OF BACTERIAL BIOFILMS

(75) Inventors: John F. Kokai-Kun, Frederick, MD (US); Julie M. Adams, Columbia, MD (US); James J. Mond, Silver Spring, MD (US); Scott M. Walsh, Germantown, MD (US); Anjali G. Shah, North Potomac, MD (US); Tanya I. Chanturiya, Gaithersburg, MD (US)

(73) Assignee: Biosynexus Incorporated, Gaithersburg, MD (US)

( * ) Notice: Subject to any disclaimer, the term of this patent is extended or adjusted under 35 U.S.C. 154(b) by 319 days.

(21) Appl. No.: 10/401,342

(22) Filed: Mar. 26, 2003

(65) Prior Publication Data
US 2003/0215433 A1 Nov. 20, 2003

Related U.S. Application Data

(60) Provisional application No. 60/367,819, filed on Mar. 26, 2002.

(51) Int. Cl.
*A61K 38/46* (2006.01)
(52) U.S. Cl. .................................................. 424/94.6
(58) Field of Classification Search .............. 424/94.63, 424/94.6
See application file for complete search history.

(56) References Cited

U.S. PATENT DOCUMENTS

| 4,179,337 | A | 12/1979 | Davis et al. ............... 435/181 |
| 4,847,325 | A | 7/1989 | Shadle et al. ............. 525/54.1 |
| 4,931,390 | A | 6/1990 | Recsei ...................... 435/183 |
| 4,980,163 | A | 12/1990 | Blackburn et al. ........ 424/94.63 |
| 5,219,564 | A | 6/1993 | Zalipsky et al. .......... 424/78.17 |
| 5,234,903 | A | 8/1993 | Nho et al. ................. 514/6 |
| 5,760,026 | A | 6/1998 | Blackburn et al. ........ 514/192 |
| 5,820,607 | A | 10/1998 | Tcholakian et al. ....... 604/265 |
| 5,858,962 | A | 1/1999 | Blackburn et al. ........ 514/2 |
| 6,028,051 | A | 2/2000 | Climo et al. .............. 514/2 |
| 6,315,996 | B1 | 11/2001 | O'Callaghan ............ 424/94.63 |
| 7,151,139 | B2 * | 12/2006 | Tiller et al. .............. 525/165 |
| 2002/0006406 | A1 | 1/2002 | Goldstein et al. ........ 424/165.1 |
| 2002/0037260 | A1 * | 3/2002 | Budny et al. ............. 424/49 |
| 2003/0229000 | A1 * | 12/2003 | Merritt et al. ............ 514/1 |

FOREIGN PATENT DOCUMENTS

WO 01/04287 A1 1/2001

OTHER PUBLICATIONS

Gander et al. "An investitation of the antimicrobial effects of linezolid on bacterial biofilms utilizing an in vitro pharmacokinetic model" J. Antimicrobial Chemotherapy (2002) 49: 301-308.*
Christensen et al. "Adherence of Coagulase-negative staphylococci to plastic . . ." J. Clin. Microbiol. (1985) 22(6): 996-1006.*
S. Zalipsky, "Functionalized Poly (ethylene glycol) for Preparation of Biologically Relevant Conjugates," *Bioconjugate Chem.*, 6, 150-165 (1995).
A. Thierry, S. Pinaud, N. Bigler, G. Perrenoud, B. Denis, M. Roggero, N. Fasel, C. Moulon, S. Demotz, "Long Synthetic Peptides as Biologically Active Proteins: The Example of the Chemokines," *Biologicals*, 29 (3-4), 259-263 (2001).
H. Gaertner, R. Offord, "Site-Specific Attachment of Functionalized Poly (ethylene glycol) to the amino Terminus of Proteins," *Bioconjugate Chem.*, 7, 38-44 (1996).
International Search Report for PCT/US03/09354, issued Aug. 21, 2003.

* cited by examiner

*Primary Examiner*—Sandra Saucier
*Assistant Examiner*—Susan Hanley
(74) *Attorney, Agent, or Firm*—Casimir Jones S.C.

(57) ABSTRACT

Methods for treating patients in which damaged tissue or an indwelling prosthetic device or catheter has a bacterial biofilm growing thereon, to at least partially disrupt said biofilm, by administering at least one antibacterial enzyme that is lethal or damaging to the biofilm-forming bacteria in an amount that is effective to at least partially disrupt the biofilm upon contact therewith. Methods for prophylactically treating a patient, and methods for disinfecting or sterilizing a surface ex-vivo to remove a biofilm or prevent biofilm growth are also disclosed, as well as implantable articles susceptible to biofilm growth to which a prophylactic coating of an antibacterial enzyme has been applied.

50 Claims, 10 Drawing Sheets

ANTIBIOTIC CONCENTRATION

ANTIBIOTIC CONCENTRATION

ENZYME DISRUPTION OF BACTERIAL BIOFILMS

CROSS-REFERENCE TO RELATED APPLICATION

The present application claims priority benefit under 35 U.S.C. §119(e) of U.S. Provisional Application Serial No. 60/367,189 filed on Mar. 26, 2002, the disclosure of which is incorporated herein by reference.

BACKGROUND OF THE INVENTION

1. Field of the Invention

This invention pertains to the disruption of bacterial biofilms with antibacterial enzymes. More specifically, this invention relates to the disruption of staphylococcal biofilms with lysostaphin.

2. Background Art

A. Biofilms

Bacteria that adhere to implanted medical devices or damaged tissue can encase themselves in a hydrated matrix of polysaccharide and protein and form a slime layer also known as a biofilm. Biofilms pose a serious problem for public health because of the increased resistance of biofilm-associated organisms to antimicrobial agents and the association of infections with these organisms in patients with indwelling medical devices or damaged tissue. Antibiotic resistance of bacteria growing in biofilms contributes to the persistence and chronic nature of infections such as those associated with implanted medical devices. The mechanisms of resistance in biofilms are different from the now familiar plasmids, transposons, and mutations that confer innate resistance to individual bacterial cells. In biofilms, resistance seems to depend on multicellular strategies.

Biofilms are complex communities of microorganisms attached to surfaces or associated with interfaces or damaged tissue. Despite the focus of modern microbiology research on pure culture, planktonic (free-swimming) bacteria, it is now widely recognized that most bacteria found in natural, clinical, and industrial settings persist in association with surfaces as biofilms. Furthermore, these microbial communities are often composed of multiple species that interact with each other and their environment. The determination of biofilm architecture, particularly the spatial arrangement of microcolonies (clusters of cells) relative to one another, has profound implications for the function of these complex communities.

The biofilm matrix is a dynamic environment in which the component microbial cells appear to reach homeostasis and are optimally organized to make use of all available nutrients. The matrix therefore shows great microheterogeneity, within which numerous microenvironments can exist. Biofilm formation is believed to be a two-step process in which the attachment of bacterial cells to a surface is followed by growth dependent accumulation of bacteria in multilayered cell clusters. Although exopolysaccharides provide the matrix framework, a wide range of enzyme activities can be found within the biofilm, some of which greatly affect structural integrity and stability.

More specifically, during the first phase of formation, it is hypothesized that the fibrinogen and fibronectin of host plasma cover the surface of a medical implant or damaged tissue and are identified by constitutively expressed microbial surface components, which mediate the initial attachment of bacteria to the surface of the biomaterial or damaged tissue. In the second step, a specific gene locus in the bacteria cells, called the intracellular adhesion (ica) locus, activates the adhesion of bacteria cells to each other, forming the secondary layers of the biofilm. The ica locus is responsible for the expression of the capsular polysaccharide operon, which in turn activates polysaccharide intercellular adhesion (PIA), via the sugar poly-N-succinylglucosamine (PNSG), a-1,6-linked glucosaminoglycan. The production of this polysaccharide layer gives the biofilm its slimy appearance when viewed using electron microscopy.

*Staphylococcus aureus* is a highly virulent human pathogen. Both *S. aureus* and coagulase-negative staphylococci have emerged as major nosocomial pathogens associated with biofilm formation on implanted medical devices and damaged tissue. These organisms are among the normal carriage flora of human skin and mucous membranes, making them prevalent complications during and after invasive surgery or prolonged hospital stays. As bacteria carried on both healthy and sick people, staphylococci are considered opportunistic pathogens that invade patients via open wounds and via biomaterial implants.

Biofilm infections associated with *S. aureus* are a significant cause of morbidity and mortality, particularly in settings such as hospitals, nursing homes and infirmaries. Patients at risk include infants, the elderly, the immuno-compromised, the immuno-suppressed, and those with chronic conditions requiring frequent hospital stays. Patients with intravascular and other implanted prosthetic devices are at even greater risk from staphylococcal infections because of compromised immune systems and the introduction of foreign bodies, which serve to damage tissue and/or act as a surface for the formation of biofilms. Such infections can have chronic, if not fatal, implications.

Catheter related infections continue to be a significant source of morbidity and mortality in patients requiring catheterization. The reported incidence in the United States is 4%, which equates to 200,000 patients per year. Additionally, catheter related infections have an attributable mortality of 14-24% and increase medical expenses by prolonging hospitalization. As a result, prevention or even reduction in the incidence of these catheter-related infections could have a significant healthcare benefit.

Catheter infections are most commonly caused by staphylococci, either coagulase negative staphylococci (CoNS) or *S. aureus*. Infections caused by CoNS can be mild and some can be treated by either removing the catheter or a course of antibiotics with the catheter in place. *S. aureus* infections are usually more severe and require removal of the catheter or other prosthetic device in addition to extended antibiotic therapy.

*S. aureus* is a prodigious toxin producer and a highly virulent human pathogen. It is the cause of a variety of human diseases, ranging from localized skin infections to life-threatening bacteremia and infections of vital organs. If not rapidly controlled, a *S. aureus* infection can spread quickly from the initial site of infection to other organs. Although the foci of infection may not be obvious, organs particularly susceptible to infection include the heart valves, kidneys, lungs, bones, meninges and the skin of burn patients.

While effective antimicrobial agents against antibiotic-susceptible staphylococcal infections have been developed, agents are still needed that consistently and thoroughly kill antibiotic-resistant *S. aureus* especially those associated with biofilms, on implanted prosthetic devices and on damaged tissue, to eliminate this source of persistent and chronic staphylococcal infections. Unfortunately, *S. aureus* in biofilms (even those which are antibiotic-susceptible in the planktonic state) tend to be less susceptible to antibiotics and thus a more difficult infection to clear.

The causes of biofilm resistance to antibiotics may include, the failure of some antimicrobial agents to penetrate all the layers of a biofilm, the slow-growth rate of certain biofilm cells that make them less susceptible to antimicrobial agents requiring active bacterial growth, and the expression of gene patterns by the bacterial cells embedded in the biofilm that differ from the genes expressed in their planktonic (free-swimming) state. These differences in biofilm-associated bacteria render antimicrobial agents that work effectively to kill planktonic bacteria ineffective in killing biofilm-associated bacteria. Often the only way to treat catheters or prosthetic devices with associated biofilms is the removal of the contaminated device, which may require additional surgery and present further risks to patients.

Coating catheters on other prosthetic devices with antimicrobial agents is a promising approach for the control and prevention of these foreign body related infections. Currently, six types of antiseptic catheters have been tested in clinical trials: cefazolin, teicoplanin, vancomycin, silver, chlorohexidine-silver sulfadiazine and minocycline-rifampin coated catheters. However, only the minocycline-rifampin coated catheters have been shown to reduce the incidence of catheter related bloodstream infections (CRBI's), and its long-term efficacy has not been investigated. There is a clear need to find a new antimicrobial agent with properties that improve catheter durability by decreasing CRBI's and an agent that has the capacity to clear biofilm associated staphylococcal infections in place, be they on catheters, prosthetic devices or damaged tissue, without requiring surgical removal.

B. Lysostaphin

One such anti-microbial agent that was originally believed to be ineffective against biofilms is lysostaphin. Lysostaphin is a potent antibacterial enzyme first identified in *Staphylococcus simulans* (formerly known as *S. staphylolyticus*). A bacterial glycylglycine endopeptidase, lysostaphin is capable of cleaving the specific cross-linking polyglycine bridges in the cell walls of staphylococci, and is therefore highly lethal to both actively growing and quiescent staphylococci. Expressed in a single polypeptide chain, lysostaphin has a molecular weight of approximately 27 kDa.

Lysostaphin is particularly effective in lysing *S. aureus* because the cell wall bridges of *S. aureus* contain a high proportion of glycine. Lysostaphin has also demonstrated the ability to lyse *Staphylococcus epidermidis*, the most prevalent coagulase-negative bacterial infection found in hospital settings. However, because of the complexity of biofilm architecture and the mechanism by which lysostaphin lyses staphylococci, lysostaphin was not expected to be effective against staphylococci in established biofilms.

U.S. Pat. No. 6,028,051 to Climo, et al., discloses a method for the treatment of staphylococcal disease with lysostaphin. Relatively high doses of lysostaphin, of at least 50, preferably 100, milligrams of lysostaphin per kilogram of body weight are used for treatment. Lysostaphin can be used in single dose treatments or multiple dose treatments, as well as singularly or in combination with additional antibiotic agents. The '051 patent also discloses that the cloning and sequencing of the lysostaphin gene permits the isolation of variant forms that can have properties similar to or different from those of wild type lysostaphin.

U.S. Pat. No. 6,315,996 to O'Callaghan, discloses a method for using lysostaphin as an effective antibiotic for topical treatment of staphylococcus corneal infections. U.S. Pat. No. 5,760,026 to Blackburn et al., discloses a method for using lysostaphin to eliminate and cure staphylococcal infections including the cure of mastitis in dairy cows by intramammary infusion.

U.S. Published Patent Application No. 2002/0006406 filed by Goldstein et al. discloses that low doses of lysostaphin, on the order of 0.5 to 45 mg/kg/day, and its analogues such as variants and related enzymes, are "sufficient" to eradicate most staphylococcal infections, including those "associated with" a catheter or prosthetic device. Thus, there is no disclosure in this or the other publications to lead one skilled in the art to expect lysostaphin to be effective for disrupting biofilms of staphylococcal or other bacterial origin established on the surface of implanted prosthetic devices, catheters or damaged tissue. It should be noted that, not all bacteria "associated with" a catheter or prosthetic device are in biofilms, and not all biofilms are "associated with" catheters or prosthetic devices.

SUMMARY OF THE INVENTION

It has now been discovered that antibacterial enzymes such as lysostaphin unexpectedly not only kill all bacteria in a biofilm, they also disrupt the biofilm matrix completely, eradicating it from the surface on which it has formed. This makes possible the treatment of biofilm-related infections, especially those that form on damaged tissue or on the surfaces of indwelling prosthetic devices and catheters, without resorting to surgical removal.

Therefore, according to one aspect of the present invention, a method is provided for treating a patient in whom damaged tissue or an indwelling prosthetic device or catheter has a bacterial biofilm growing thereon, to at least partially disrupt said biofilm thereon, comprising administering to said patient at least one antibacterial enzyme that is lethal or damaging to the biofilm-forming bacteria in an amount that is effective to at least partially disrupt the biofilm upon contact therewith. For staphylococcal and other bacterial-based biofilms, lysostaphin and lysostaphin analogues have proven to be particularly effective in both preventing biofilm growth and eradicating biofilms that are already established.

The present invention also includes the prophylactic administration of antibacterial enzymes to prevent biofilm growth in a susceptible patient with tissue damage or a prosthetic device or catheter. Therefore, according to another aspect of the present invention, a method is provided for preventing biofilm growth in a susceptible patient by administering a prophylactically effective amount of an antibacterial enzyme that is lethal or damaging to a biofilm-forming bacteria. For example, lysostaphin and lysostaphin analogues may be administered prophylactically to prevent the growth of staphylococcal biofilms in patients susceptible thereto.

The present invention also includes the disinfection or sterilization of ex-vivo surfaces not necessarily intended for patient contact. That is, the method of the present invention is suitable for disinfecting or sterilizing essentially any surface, including anything implantable into the body such as polymers and metals such as titanium, on which the growth of a biofilm has occurred, or on which the growth is possible but undesirable. For practical purposes, the inventive method will be primarily used in those circumstances where more rigorous sterilization or disinfection conditions used for biofilm removal or prevention are unsuitable, including situations where residual traces of the harsh chemicals employed would be harmful. Thus, the method of the present invention is particularly useful for preventing biofilm growth on a surface intended for medical implants in a patient or eliminating contamination before biofilm formation begins.

Therefore, according to another aspect of the present invention a method is provided for disinfecting or sterilizing a surface ex-vivo, with a bacterial biofilm growing thereon, to at least partially remove the biofilm therefrom, in which the surface is contacted with at least one antibacterial enzyme that is lethal or damaging to the biofilm-forming bacteria in an amount that is effective to at least partially disrupt the biofilm upon contact therewith. This aspect of the present invention is particularly effective for disinfecting or sterilizing surfaces to prevent or remove the growth of a biofilm.

The present invention also includes ex-vivo methods for preventing the growth of a biofilm on a susceptible surface. Therefore, according to another aspect of the present invention, a method is provided for disinfecting, protecting or sterilizing a surface ex-vivo to prevent biofilm-forming bacteria from growing thereon, by contacting the surface with a prophylactically effective amount of at least one antibacterial enzyme that is lethal or damaging to a biofilm-forming bacteria. The aspect of the present invention is particularly effective for disinfecting, protecting or sterilizing surfaces susceptible to biofilm growth and intended for medical implantation into a patient, such as catheters and prosthetic devices.

Antibacterial enzymes such as lysostaphin are ionically charged in situ to the extent that they have a tendency to adhere to surfaces, especially polymeric surfaces. Thus, surfaces treated therewith retain a coating of the enzyme that serves to maintain the disinfected or sterile state in vivo and prevent biofilm formation thereon. The present invention therefore further includes prosthetic devices and catheters, implantable in a patient in need thereof and having at least one surface susceptible to the growth of a bacterial biofilm, that are coated with at least one antibacterial enzyme that is lethal to a biofilm-forming bacteria in an amount effective to prevent biofilm formation.

The coating may be physically retained by the ionic charge of the enzyme. For a polymeric surface, the coating may be retained by covalent attachment of the enzyme to the polymeric surface, or it may be blended with a surface polymer by techniques that result in presentation of the enzyme at the polymer surface without substantial release therefrom. The present invention thus further includes methods for preparing polymer compositions resistant to the growth of a bacteria biofilm on a surface formed therefrom by blending the polymer with an effective amount of at least one antibacterial enzyme that is lethal to a biofilm-forming bacteria. The invention also includes polymer compositions for fabrication of a prosthetic device or catheter in which the polymer is blended with at least one antibacterial enzyme that is lethal to a biofilm-forming bacteria in an amount that is effective to prevent biofilm formation on a surface formed therefrom.

Examples of prosthetic devices include essentially any device intended for insertion into a body, which include, but are not limited to, shunts, stents, scaffolds for tissue construction, gastric feeding tubes, punctual plugs, artificial joints, pacemakers, artificial valves, and the like. The definition is intended to include essentially any surface on which there is a risk that the growth of a bacterial biofilm may occur.

The foregoing and other objects, features and advantages of the present invention are more readily apparent from the detailed description set forth below, taken in conjunction with the accompanying drawings.

DETAILED DESCRIPTION

Figure 1A:
FIG. 1 is a SEM photograph at two levels of magnification (2000× on left and 660× on right) depicting S. aureus biofilm growth on tissue culture inserts that were not treated with lysostaphin.

The present invention treats and prevents bacterial biofilm infections with antibacterial enzymes. For purposes of the present invention, the term "biofilm infection" is defined as the formation of a biofilm upon damaged tissue or the surface of an indwelling catheter or prosthetic device susceptible thereto. This definition is in distinction to, and excludes, the persistent and chronic infections that are secondary to the formation of a biofilm within a patient. These secondary infections may respond temporarily to conventional treatment and to dosages of the antibacterial enzymes of the present invention that may not be effective to eliminate the biofilm completely.

"Antibacterial enzyme" is defined according to the meaning given to this term by those of ordinary skill in the art, and refers to any proteolytic, pore-forming, degradative or inhibitory enzyme that kills or damages a bacterial species or particular strain thereof. The result may be achieved by damaging the cell wall of the bacteria, disrupting cell membranes associated with the cell wall or within the bacteria, inhibiting protein synthesis within the bacteria, disrupting the sugar backbone, or by any other mechanism attributed to a peptide or protein considered by those skilled in the art to be an antibacterial enzyme. The enzyme may be a natural, wild-type enzyme, modified by conventional techniques, conjugated to other molecules, recombinantly expressed, or synthetically constructed.

This is not an unlimited class of materials. After learning from the present specification that applicants have discovered the ability of antibacterial enzymes to both kill bacteria and disrupt biofilms based thereon, those of ordinary skill in the art can readily identify suitable enzymes for use in the present invention without undue experimentation. One example of an antibacterial enzyme is lysostaphin. Lysostaphin is important because it is effective in the treatment of staphylococci and biofilms formed therefrom. "Lysostaphin," and "lysostaphin analogues" are defined as including lysostaphin (wild type), any lysostaphin mutant or variant, any recombinant, or related enzyme (analogue) or any synthetic version or fragment of lysostaphin (whether synthetic or otherwise) that retains the proteolytic ability, in vivo and in vitro, to cleave the cross-linked polyglycine bridges in the cell wall peptidoglycan of staphylococci. The enzymes may be generated by post-translational processing of the protein (either by enzymes present in a producer strain or by means of enzymes or reagents introduced at any stage of the process) or by mutation of the structural gene. Mutations may include site deletion, insertion, domain removal and replacement mutations.

The lysostaphin of the present invention may be synthetically constructed, expressed in mammalian cells, insects, bacteria, yeast, reptiles or fungi, recombinantly expressed from a cell culture or higher recombinant species such as a mouse, or otherwise. This would include the activity-retaining synthetic construction including synthetic peptides and polypeptides or recombinant expression of portions of the lysostaphin enzyme responsible for its activity against staphylococci as part of a larger protein or peptide, include chimeric proteins, containing the active sites of one or more other antibacterial enzymes that are effective either against staphylococci or other biofilm-forming bacteria species.

The recombinant expression of homogenous lysostaphin, and homogenous fully active lysostaphin-containing compositions prepared from the expressed protein are disclosed in a U.S. Patent Application entitled "Lysostaphin Molecule with Enhanced Staphylolytic Activity," filed by Jeffery Richard Stinson, Lioubov Grinberg, Jon Kokai-Kun, Andrew Lees and James Jacob Mond on Dec. 21, 2002, the disclosure of which is incorporated herein by reference in its entirety. The application claims priority from U.S. Provisional Application No. 60/341,804 filed Dec. 21, 2001.

Effective pharmaceutical formulations of the antimicrobial enzymes include aqueous solutions or dry preparations (e.g., lyophilized crystalline or amorphous, with or without additional solutes for osmotic balance) for reconstitution with liquids suitable for parenteral delivery of the active agent. Formulations may be in, or be reconstituted in, small volumes of liquids suitable for bolus iv, im or peripheral injection or by addition to a larger volume iv drip solution, or may be in, or reconstituted in, a larger volume to be administered by slow iv infusion.

Delivery is preferably via intravenous (iv), intramuscular, subcutaneous or intraperitoneal routes or intrathecally or by inhalation, or by direct instillation into an infected site (or, for prevention purposes, the site of tissue damage or an indwelling catheter or prosthetic device susceptible to biofilm formation), so as to permit blood and tissue levels in excess of the minimum inhibitory concentration (MIC) or minimum bactericidal concentrations (MBC) of the active agent to be attained and thus to effect a reduction in bacterial titers, to disrupt a biofilm that has formed, or to inhibit potential biofilm formation.

When the antimicrobial enzymes of the present invention are specific to bacteria species, or in some circumstances, to one or more strains thereof, the pharmaceutical preparations may contain a plurality of the enzymes to produce a broad spectrum activity against biofilm infections. The antimicrobial enzymes of the present invention, however, may be administered alone to treat biofilm infections against which their efficacy under such circumstances has been demonstrated.

Suitable dosages and regimes of the antimicrobial enzyme may vary with the species of the patient, the severity of the biofilm infection, the sensitivity of the infecting organism and, in the case of combination therapy, may depend on the particular antibacterial agent(s) used in combination. Candidate patient species are not limited to humans, but include essentially all cold- or warm-blooded vertebrate species suffering from or at risk for a biofilm infection that would benefit from treatment with an antimicrobial enzyme. Dosages may range from about 0.1 to about 100 mg/kg/day, and typically from about five to about 50 mg/kg/day, given as single or divided doses. The doses can be given by many means, including by continuous infusion or divided into a plurality of dosages per day. For the prevention of biofilm formation, lower dosages may be effective.

Furthermore, the antibacterial enzymes can be coadministered, simultaneously or alternating, with other antimicrobial agents so as to more effectively disrupt the biofilm and prevent its reoccurrence. For example, lysostaphin and its analogues can be administered in conjunction with antibiotics that interfere with or inhibit cell wall synthesis, such as penicillin, nafcillin, oxacillin, and other β-lactam antibiotics, cephalosporins such as cephalothin, glycopepetides such as vancomycin and other polypeptides. Or, lysostaphin and its analogues can be administered in conjunction with antibiotics that inhibit protein synthesis such as aminoglycosides like streptomycin, tetracyclines and streptogramins. Lysostaphin and its analogues may also be administered with monoclonal antibodies; or other antibacterial enzymes such as lysozyme, mutanolysin, and cellozyl muramidase; peptides such as defensins; and lantibiotics such as nisin; or any other lanthione-containing molecules, such as subtilin. Anti-staphylococcal agents to be coadministered with lysostaphin and lysostaphin analogues may be formulated together therewith as a fixed combination or may be used extemporaneously in whatever formulations are available and practical and by whatever routes of administration are known to provide adequate levels of these agents at the sites of infection.

The antibacterial enzymes may also be coated on the surface of a metal or plastic catheter or prosthetic device for implantation having at least one surface susceptible to biofilm formation by immersion of the catheter or device in a solution of the enzyme for a length of time sufficient to form a biofilm-formation inhibiting coating of the enzyme on the susceptible surface. Even the most minimal concentration of enzyme will confer some protection. Typically, a concentration of from about 10 µg/ml to about 100 mg/ml can be used. With device surfaces, the coatings may also be formed by covalent attachment of the enzyme thereto. With polymeric devices, it may be blended with a surface polymer by techniques that result in sequestration or localization of the enzyme at the surface without substantial release therefrom. Lysostaphin and other inhibitory factors may also be directly introduced through catheters and indwelling devices, either before implantation or after implantation, at a rate that is conducive to lysostaphin and the other inhibitory factors coating the surface of the device or catheters to be protective against biofilm formation. This rate of introduction may include, filling the catheters with lysostaphin and other inhibitory factors and sealing the catheter to allow time for the lysostaphin and other factors to coat the catheter surface; or pumping lysostaphin and other factors through the catheter, either in an enclosed loop or through the implanted catheter at a rate which allows the lysostaphin and other factors to coat the catheter. These techniques are well known to those skilled in the art of indwelling device fabrication and require no further description.

The present invention is further illustrated by the following examples that teach those of ordinary skill in the art how to practice the invention. The following examples are merely illustrative of the invention and disclose various beneficial properties of certain embodiments of the invention. The following examples should not be construed as limiting the invention as claimed.

EXAMPLES

Example 1

Disruption of *S. aureus* Biofilms with 100 µg/1 ml Lysostaphin in vitro

Staphylococcal strains were stored in ~0.5 mL Tryptic Soy Broth (TSB, Difco Bacto) aliquots at −70° C. Prior to each experiment, an aliquot was taken from the freezer, plated on sheep's blood agar (Remel), and incubated at 37° C. overnight.

TABLE 1

Bacteria strains used:

| Species | Designation | Information |
|---|---|---|
| S. aureus | ATCC 49521 (SA5) | type 5 capsule |
| S. aureus | Col | MRSA |
| S. aureus | Col-lysoR | Lysostaphin-resistant variant of above |
| S. aureus | MBT 5040 | MRSA |
| S. aureus | MBT 5040 lysoR | Lysostaphin-resistant variant of above |
| S. aureus | ATCC 35556 | wild type for below |
| S. aureus | dltA negative | does not make biofilm |
| S. epidermidis | SE 380 | Clinical Isolate |
| S. epidermidis | HAY | Clinical Isolate |
| S. epidermidis | SE 1175 | Clinical Isolate |
| S. epidermidis | ATCC 35984 | High slime producer |

Biofilm Assay

Five ml of TSB supplemented with 0.25% glucose (Sigma-Aldrich) was inoculated with five isolated staphylococcal colonies. The cultures were incubated at 37° C. overnight with shaking.

The overnight cultures were adjusted to $Abs_{578}$ of 0.1 in ~3 ml PBS (BioWhittaker) using a Spectronic 20D+. One 96 well plate containing 200 µl of TSB+0.25% glucose or 24 sterile 0.02 mm Anopore Membrane polystyrene plate inserts (Nalge Nunc International) each containing 1 ml of TSB+ 0.25% glucose and fitted in a 24-well tissue culture plate (Nalge Nunc International), were inoculated with a 1:200 dilution of the adjusted overnight culture. The plates were incubated at 37° C. overnight to allow biofilms to form.

Treatment

After approximately 24 hours of growth, half of the wells or inserts were infused with 1001 µg/ml of lysostaphin (AMBI, now Nutrition21, or Biosynexus Incorporated). The plates were then incubated overnight at 37° C.

Biofilm Detection

After 48 hrs of incubation, the wells or inserts were washed gently twice with PBS. The washed 96 well plate or the 24 inserts were air dried completely at room temperature. The 96-well plate was stained with safranin (Remel) to detect biofilms, while the inserts were fixed with a 3× glutaraldehyde buffer (0.7M NaCl, 0.014M KCl, 0.007M $KH_2PO_4$, 0.039M $Na_2HPO_4$, 1M OHC $(CH_2)_{3CHO}$) in preparation for scanning electron microscopy (SEM).

Figure 1B:
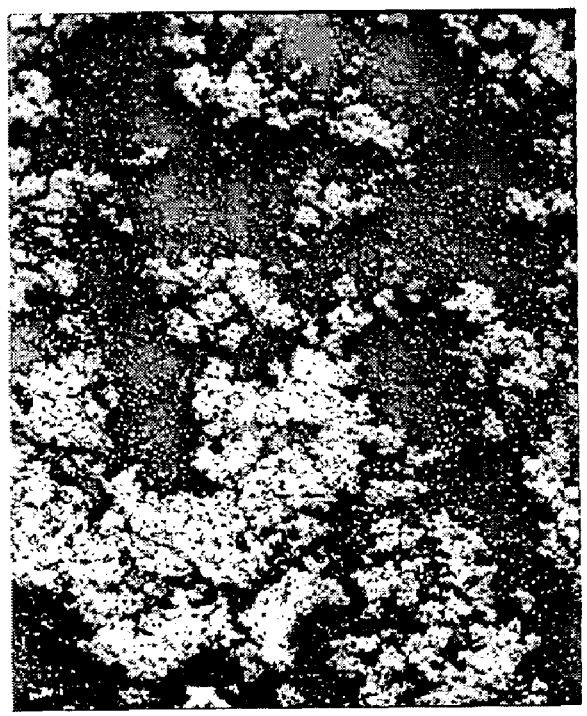

FIG. 1 is a SEM photograph at two levels of magnification (2,000× and 660×) depicting biofilm growth on the inserts that were not treated with lysostaphin.

Figure 2A:
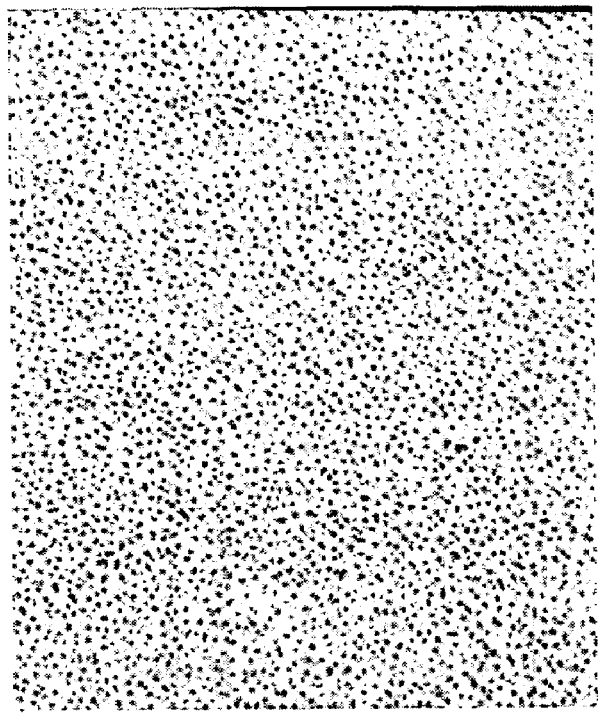
FIG. 2 is a SEM photograph at 6,600× on left and 660× on right magnification depicting inserts that were treated with lysostaphin; all S. aureus biofilm has been eradicated.
Figure 2B:
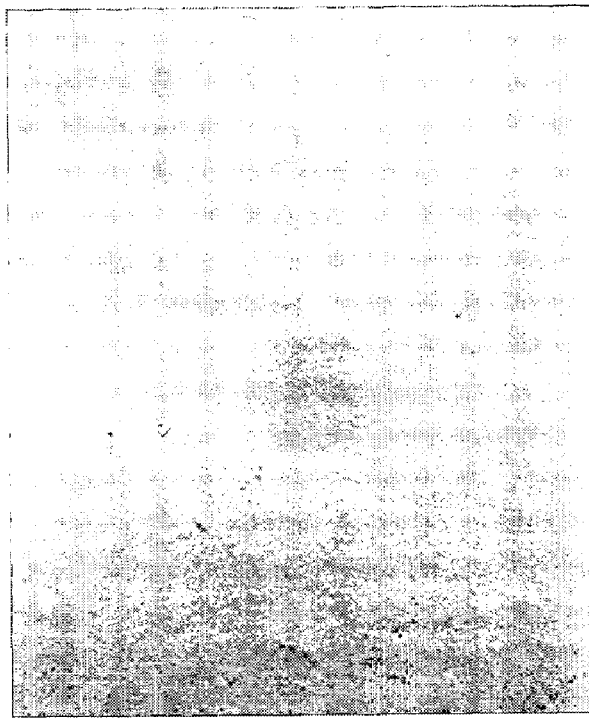

FIG. 2 is a SEM photograph at 6,600× and 660× magnification depicting inserts that were treated with lysostaphin. The ability of lysostaphin to disrupt biofilm-formation after 24 hours of growth is immediately evident.

Example 2

Disruption of *S. aureus* Biofilms With 50 µg/ml Lysostaphin in vitro

Figure 3:
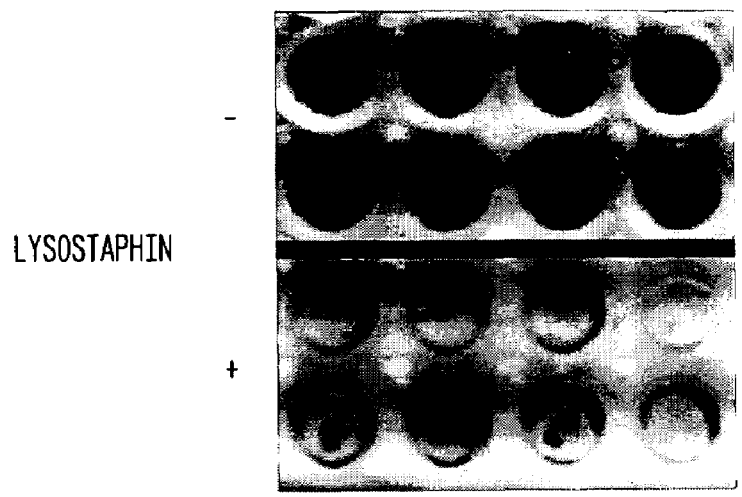
FIG. 3 depicts a scan of 16 wells of a tissue culture plate, in which S. aureus strain MBT 5040 biofilms were treated with (+) and without (−) 50 µg/ml lysostaphin, eight wells each.

Methicillin-resistant *S. aureus* strain MBT 5040 was grown overnight in TSB plus glucose as in Example 1. Twenty four hours later, a 96 well tissue culture plate containing 200 µl TSB plus glucose was inoculated with a 1:200 dilution of the overnight culture, also as in Example 1. The 96 well plate was incubated overnight at 37° C. with shaking and transferred to a stationary 37° C. incubator for an additional 24 hours. After the second incubation, the wells were washed twice with PBS to remove planktonic cells and incubated for three hours at room temperature with either PBS without lysostaphin (−) or PBS containing 50 µg/ml lysostaphin (+). Following another three hour incubation, the wells were washed twice with PBS and then fixed in Bouin's solution (Sigma-Aldrich) for five minutes. The wells were stained with safranin for one minute and washed again with PBS. The results are depicted in FIG. 3, which demonstrates the biofilm disruption resulting from treatment with lysostaphin. The untreated wells contained biofilms, while in the treated wells the biofilms were completely disrupted.

Example 3

Preparation of Biofilm-Formation Resistant Lysostaphin-Coated Catheters

Six wells were incubated with 300 µl of either 10 mg/ml, 1 mg/ml or 100 µg/ml of lysostaphin diluted in PBS. All the samples were done in duplicates. The plate was allowed to incubate overnight at 4° C. The following morning the wells were washed with 1 ml of PBS ten times, using vacuum suction to clean out the wells. *S. aureus* strain SA5 was diluted in PBS to a percent transmittance of 40. A 1:10,000 dilution of this solution was made, and 300 µl was added to each well. The plates were put in a shaking incubator at 75 rpm for two hours at 37° C. After two hours, 40 µl from each well was taken out and plated onto a blood agar plate and put in the incubator overnight at 37° C. The colonies on the plates were counted the following morning.

Two Angiocath catheters (Becton Dickinson) were incubated with 200 PI of a 100 µg/mL solution of lysostaphin, while two others were incubated in PBS. The catheters were allowed to incubate overnight at 4° C. The following morning the catheters were washed with 50 ml PBS using a pump with a flow rate of 1.5 ml/minute. Once the catheters were washed, *S. aureus* SA5 was diluted in PBS to a percent transmittance of 40. A 1:10,000 dilution of this solution was made, and 100 µl was added to each catheter. The catheters were allowed to incubate for two hours at 37° C. Following incubation, the catheter effluent was plated onto blood agar plates and put in the incubator overnight at 37° C. The colonies on the plates were counted the following morning.

TABLE 2

| SURFACE | SAMPLE | COATING | CFU |
|---|---|---|---|
| Polystyrene | 1 | None | 625 |
| | 2 | None | 594 |
| | 1 | Lys 10 mg/ml | 2 |
| | 2 | Lys 10 mg/ml | 0 |
| | 1 | Lys 1 mg/ml | 1 |
| | 2 | Lys 1 mg/ml | 0 |
| | 1 | Lys 100 µg/ml | 4 |
| | 2 | Lys 100 µg/ml | 1 |
| Angiocath | 1 | None | 288 |
| | 2 | None | 475 |
| | 1 | Lys 100 µg/ml | 0 |
| | 2 | Lys 100 µg/ml | 0 |

Results

Lysostaphin was effectively able to kill bacteria (*S. aureus* SA5) on two different surfaces. The polystyrene surfaces were incubated with three different concentrations of lysostaphin, 10 mg/ml, 1 mg/ml and 100 µg/ml. In all three concentrations of lysostaphin, sufficient enzyme remained associated with the polymer surface to kill the added *S. aureus* in two hours at 37° C., whereas the uncoated control wells showed significantly higher bacterial counts.

The interiors of the Angiocath catheters were incubated with 100 µg/ml of a lysostaphin solution. The lysostaphin-coated catheters were able to kill *S. aureus* in two hours at 37° C., whereas the uncoated control catheters were completely ineffective at killing the bacteria in the catheters.

Comparative Example

Figure 4:
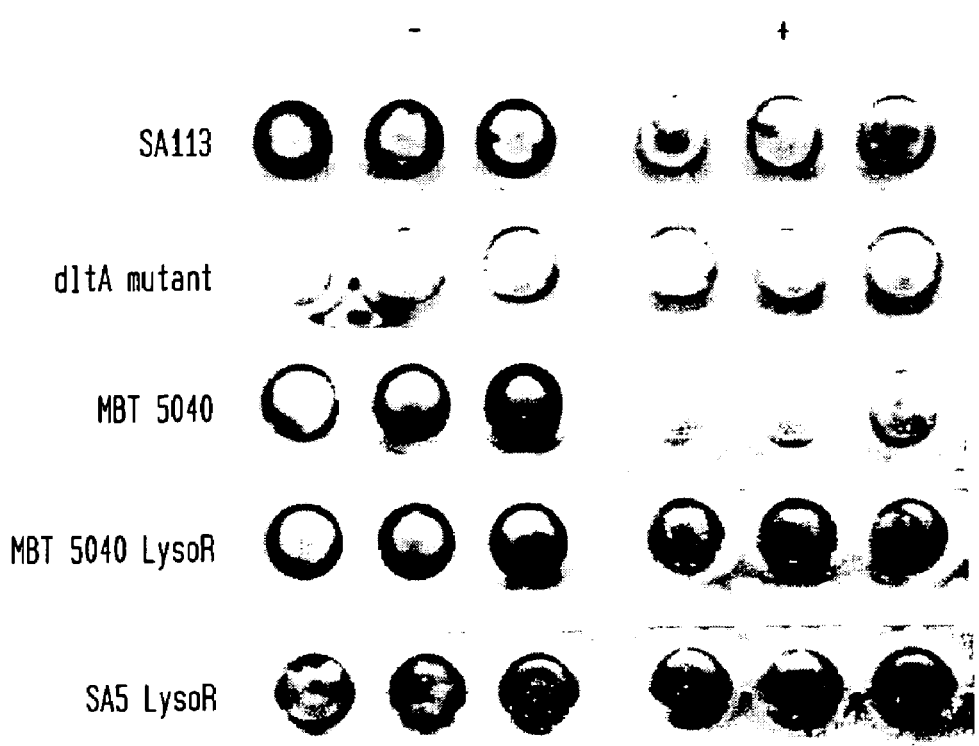
FIG. 4 depicts a scan of 30 wells of a tissue culture plate, in which biofilms of various S. aureus strains, including two lysostaphin-resistant S. aureus (LysoR) variants are treated with (+) and without (−) 50 µg/ml lysostaphin for comparison purposes.

*S. aureus* strains were grown overnight in tryptic soy broth (TSB) plus glucose. Twenty four hours later, a 96 well tissue culture plate containing 200 µl of TSB plus glucose was inoculated with a 1:200 dilution of the overnight culture. The 96 well plate was incubated overnight at 37° C. with shaking and then transferred to a stationary 37° C. incubator for an additional 24 hours. Following the second incubation, the wells were washed twice with PBS to remove planktonic cells and then incubated for three hours at room temperature with either PBS without lysostaphin (−) or PBS containing 50 µg/ml lysostaphin (+). Following the three hour incubation, the wells were washed twice with PBS and then fixed in Bouin's Solution for five minutes. The fixed wells were stained with safranin and then washed again with PBS. The failure of lysostaphin to disrupt biofilms of lysostaphin-resistant strains of *S. aureus* is shown in FIG. 4 and demonstrates the specificity of lysostaphin for bacteria that are sensitive to this enzyme. This finding also suggests that lysostaphin acts on the actual bacterial cells in the biofilm and disruption of these biofilm-associated cells are sufficient to completely disrupt biofilms.

Example 4

Figure 7:
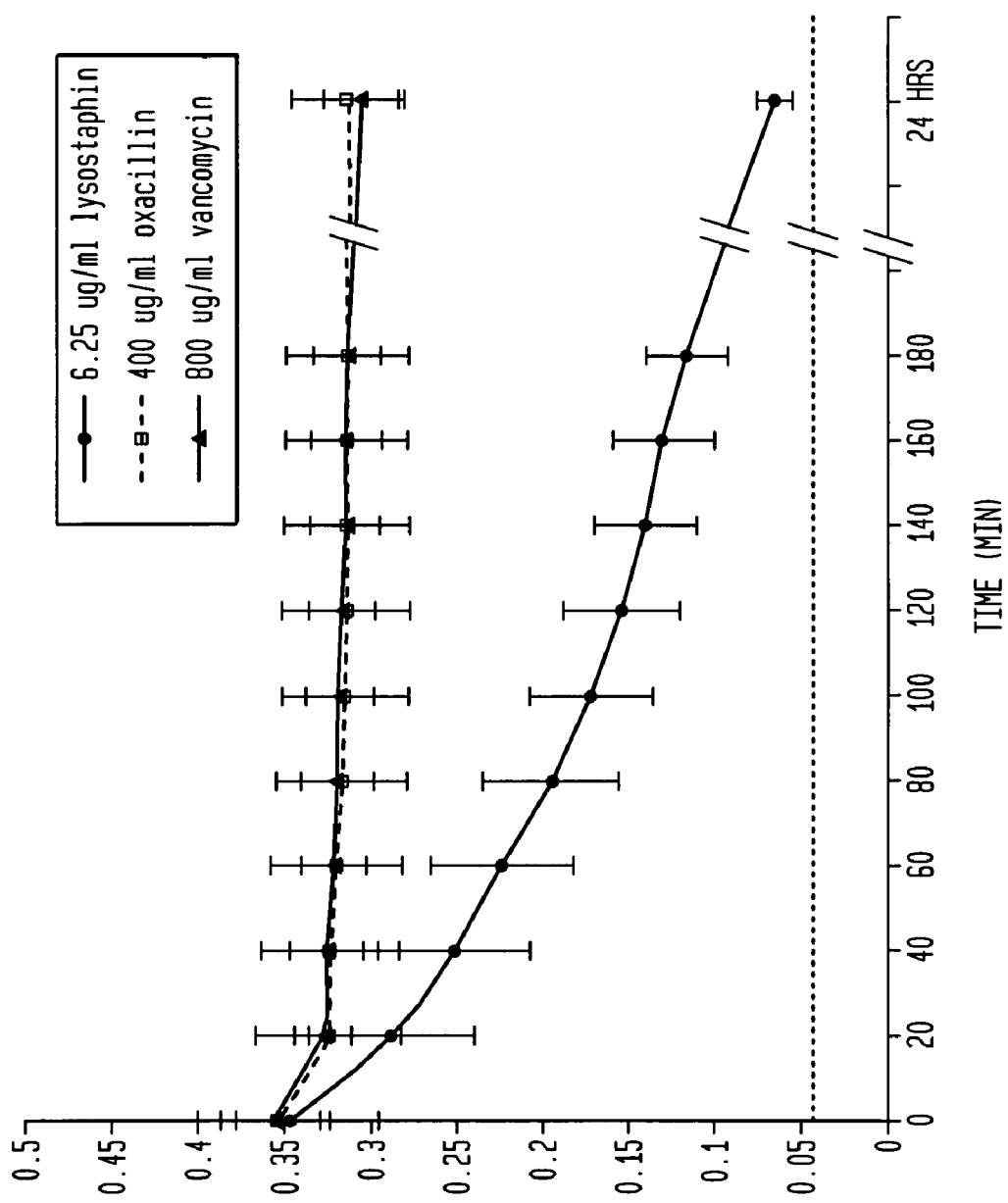
FIGS. 7 is a graph depicting lysostaphin (6.25 cg/ml) causing an immediate and continuous drop in the absorbance of S. aureus biofilms over time while vancomycin (800 cg/ml) and oxacillin (400☐cg/ml) have no effect. on the biofilms.

Lysostaphin Disrupts *S. Aureus* Biofilms Immediately and More Effectively Than Other Antibiotics Oxacillin and vancomycin have often been used in antibiotic susceptibility studies of *S. aureus* biofilms. These antibiotics were compared to lysostaphin to determine whether lysostaphin was more effective in disrupting *S. aureus* strain ATCC 35556 biofilms than conventional antibiotics. Twenty four-hour biofilms in polystyrene 96-well tissue culture plates were treated with serial dilutions of lysostaphin, oxacillin, and vancomycin (FIG. 7).

In order to examine the kinetic effect of lysostaphin, oxacillin and vancomycin on biofilms, the absorbance of established biofilms in a 96-well tissue culture plate was measured over time (0-3 hrs and 24 hrs). Tissue culture wells containing biofilms of *S. aureus* SA113 were incubated with serial dilutions of lysostaphin (0.8 g/ml-200 g/ml), oxacillin (1.6 g/ml-400 g/ml), or vancomycin (3.2 g/ml-800 g/ml) for 24 hours, and the absorbance at 650 nM was monitored every 20 minutes for the first 3 hours and then again at 24 hours. The absorbance of the lysostaphin-treated biofilms dropped from approximately 0.35 at time zero to 0.125 after 3 hours of treatment and dropped to near base line (0.04) by 24 hrs when treated with a dose of lysostaphin of 6.25 µg/ml in PBS (FIG. 7). The absorbance of the biofilms treated with oxacillin or vancomycin for twenty four hours showed minimal change with the absorbance remaining around 0.325, despite the fact that the biofilms were treated with as much as 400 µg/ml of oxacillin or 800 µg/ml of vancomycin in PBS (FIG. 7). Since antimicrobials like oxacillin or vancomycin are effective against actively metabolizing bacteria, a similar experiment was conducted but the biofilms were incubated with the three anti-microbials in bacterial media (TSB). Very similar results were also found when the assay was conducted in TSB rather than PBS. Lysostaphin reduced the absorbance of biofilms to near background by 24 hours while oxacillin and vancomycin had little or no effect even after 24 hours incubation (data not shown).

Figure 8A:
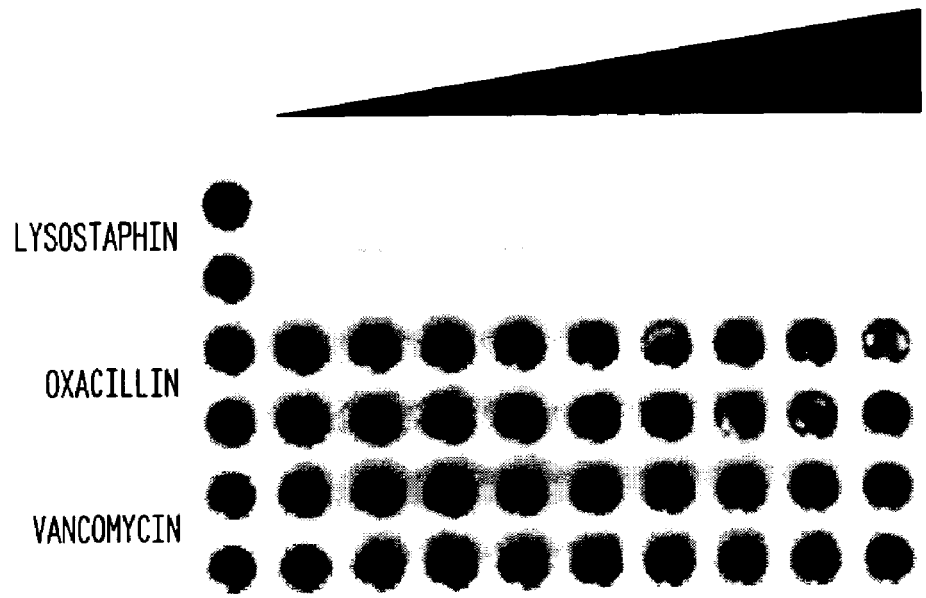
FIGS. 8A and B depicts a scan showing that oxacillin (1.6 cg/ml-400 cg/ml) or vancomycin (3.2 cg/ml-800 cg/ml) have no effect on S. aureus biofilms in PBS (A) or bacterial media (B) after twenty four hours incubation while lysostaphin in PBS cleared biofilm at 0.8 cg/ml (A) and at 12.5 cg/ml in TSB+0.25% glucose (B).
Figure 8B:
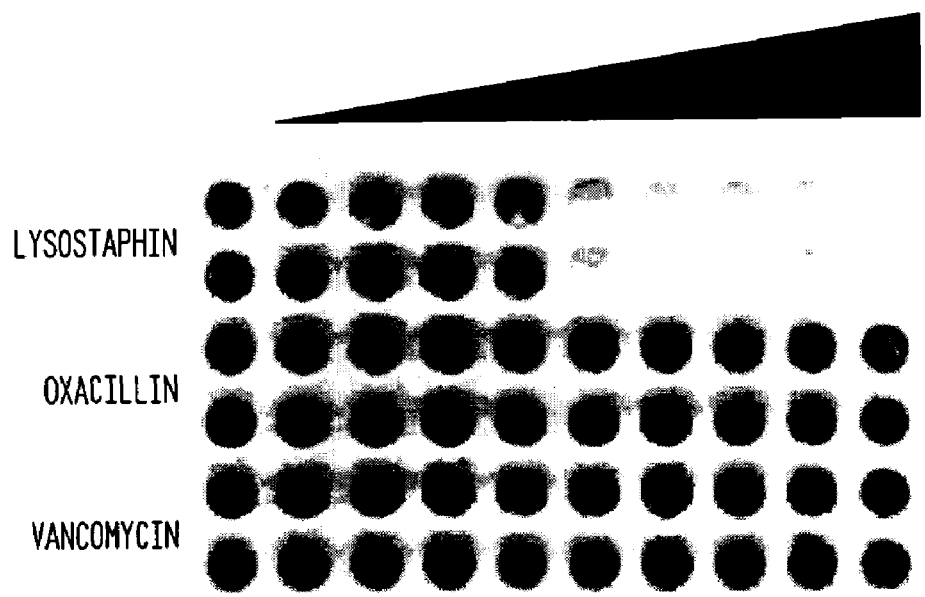

The capacity of the three agents to disrupt *S. aureus* biofilms in polystyrene wells can be visualized by comparing the staining intensity of treated wells versus control (buffer-treated) wells. Biofilms from the above described kinetics experiment treated for 24 hours stain darkly on the bottom of the wells (FIG. 8), while wells cleared of biofilms do not stain with safranin. Lysostaphin as low as 0.8 µg/ml in PBS (FIG. 8A) and 12.5 g/ml in TSB+0.25% glucose (FIG. 8B) appeared to clear biofilms from the transwells while 400 µg/ml of oxacillin or 800 µg/ml of vancomycin in PBS or TSB had no obvious effect on established biofilms even after 24 hours treatment (FIG. 8A and B).

Example 5

Lysostaphin Disrupts *S. Epidermidis* Biofilms

Figure 9:
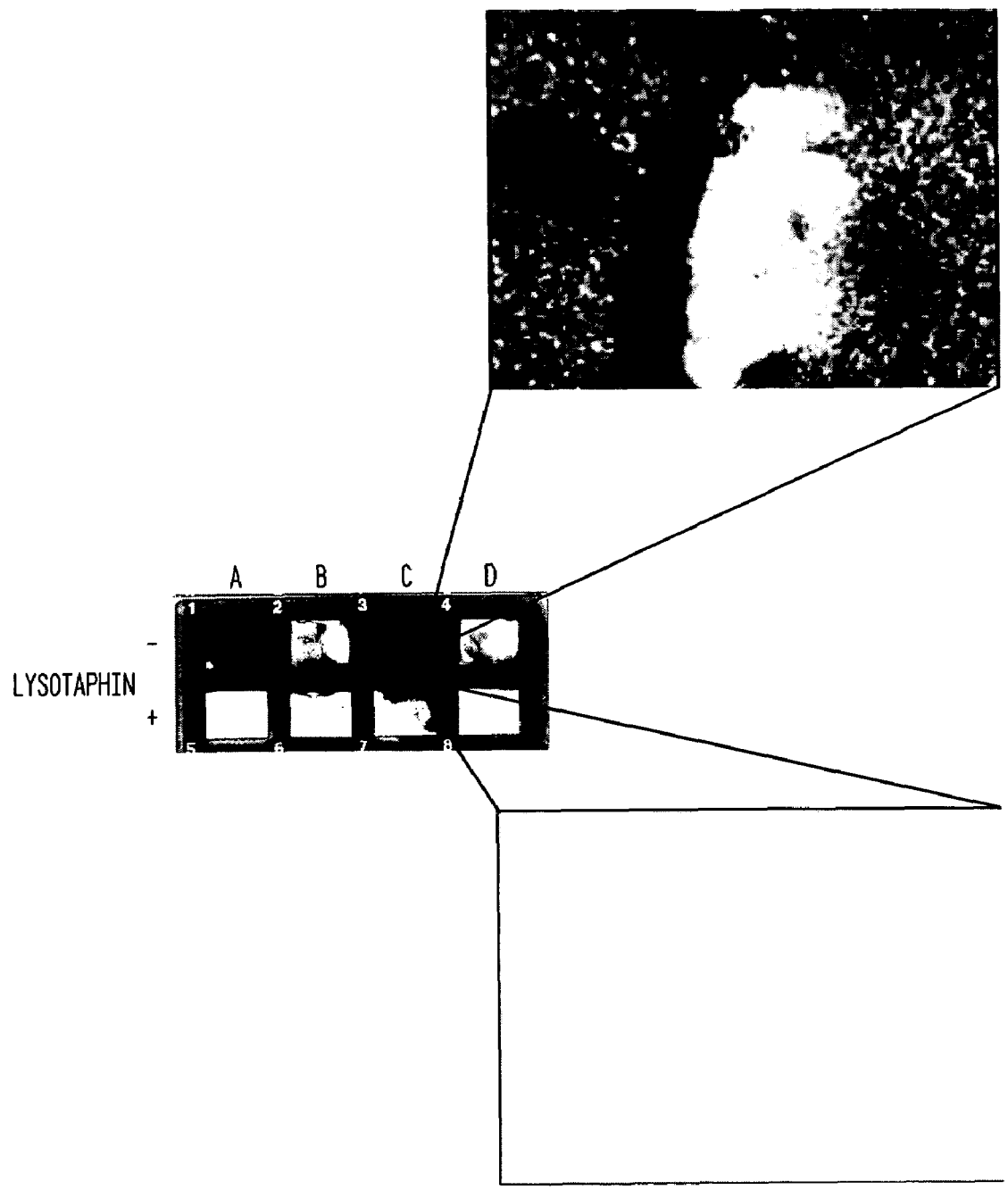
FIG. 9 depicts a scan showing that lysostaphin disrupts S. epidermidis biofilms, S. aureus SA 113 as a control (A), S. epidermidis strain Hay (B), S. epidermidis strain ATCC35984 (C) or S. epidermidis strain SE1175 (D). The two enlarged sections reveal the multi-layered biofilm of S. epidermidis strain ATCC35984 (top) and the residual glycocalyx of the same strain with no intact staphylococci following lysostaphin treatment (bottom)

While lysostaphin demonstrated activity against *S. aureus* biofilms, it was of interest to explore whether biofilms of *S. epidermidis*, known to be less sensitive to lysostaphin, were also sensitive to the biofilm disrupting effect of lysostaphin. Three *S. epidermidis* strains with various capacities for glycocalyx (slime) production were examined including, *S. epidermidis* strain Hay (a low slime producer), *S. epidermidis* strain SEI 175 (a moderate slime producer) and *S. epidermidis* ATCC 35984 (a high slime producer). All three of these *S. epidermidis* strains produced biofilms on a glass chamber slide (FIG. 9) with ATCC 35984 producing the thickest and most darkly staining biofilm as expected. Incubation of these *S. epidermidis* biofilms with 200 g/ml lysostaphin for three hours disrupted the biofilms of all three strains of *S. epidermidis* (FIG. 9). *S. aureus* strain SA113 was included in this experiment as a control. Microscopic examination of the disrupted biofilms revealed that there were no intact bacteria left associated with the artificial surface (data not shown). The stained material visible in lysostaphin treated wells is extracellular glycocalyx which stained pink by safranin and contained no intact gram positive *S. epidermidis* cells, only cellular debris.

Example 6

Treatment of Established Infection in Mice

Jugular vein catheterized mice (Charles River Labs) were used. The mice were challenged through the tail vein with *S. aureus* ($10^3$-$10^4$ CFU, a much lower dose than the $5 \times 10^6$ CFU or greater typically necessary to establish an infection in mice not catheterized). Treatment began four days post challenge when infection was established. Lysostaphin was administered through the indwelling catheter in a volume of 200 µ PBS (in the case of methicillin resistant *S. aureus*, nafcillin was added to the treatment). After the final treatment of the day, 50 µl of a lock solution (50% sterile glucose solution) with lysostaphin (and nafcillin, when used), added at the same concentration as used for treatment, was put in the catheters. Control mice received equal treatments with PBS and lock solution alone.

On the day following the last treatment the liver, heart and a portion of the catheter in the heart were harvested. The catheter portions were sonicated to release bacteria. Bacterial quantities (*S. aureus*) recovered (CFU's) are shown in Tables 3-11.

TABLE 3

| MSSA GROUP | 20 mg/kg MOUSE | t.i.d. LIVER | 4 days CATHETER |
|---|---|---|---|
| CONTROL | 1 | 239 | TNTC |
| CONTROL | 2 | TNTC | TNTC |
| CONTROL | 3 | 1494 | TNTC |
| CONTROL | 4 | TNTC | TNTC |
| LYSOSTAPHIN | 1 | 0 | 0 |
| LYSOSTAPHIN | 2 | 27 | 1 |
| LYSOSTAPHIN | 3 | 43 | 0 |
| LYSOSTAPHIN | 4 | 148 | 387* |
| LYSOSTAPHIN | 5 | 8 | 1339* |

*Lysostaphin-resistant
MSSA = Methicillin Sensitive *S. aureus*
TNTC = Too Numerous To Count

TABLE 4

| MSSA Group | 10 mg/kg Mouse | Liver | b.i.d. Heart | 4 days Catheter |
|---|---|---|---|---|
| Control | 1 | >1600 | TNTC | TNTC |
| Control | 2 | 209 | >1500 | >1600 |
| Control | 3 | 0 | 0 | 4 |

TABLE 4-continued

| MSSA Group | 10 mg/kg Mouse | Liver | b.i.d. Heart | 4 days Catheter |
|---|---|---|---|---|
| Lysostaphin | 1 | 0 | 0 | 0 |
| Lysostaphin | 2 | TNTC* | TNTC* | >1700* |
| Lysostaphin | 3 | 0 | 0 | 0 |
| Lysostaphin | 4 | 0 | 1 | 5 |
| Nafcillin (50) | 1 | 0 | 0 | 0 |
| Nafcillin | 2 | 5 | 0 | 303 |
| Nafcillin | 3 | 0 | 0 | 0 |
| Nafcillin | 4 | 0 | 0 | 3 |

*Lysostaphin-resistant

TABLE 5

| MRSA Group | 10 mg/kg+/ Mouse | Naf Liver | b.i.d. Heart | 3 days Catheter |
|---|---|---|---|---|
| Control | 1 | 1004 | 961 | TNTC |
| Control | 2 | 17 | TNTC | TNTC |
| Control | 3 | 13 | 435 | TNTC |
| Control | 4 | TNTC | TNTC | TNTC |
| Lysostaphin | 1 | 32 | 3 | 981 |
| Lysostaphin | 2 | 23 | 19 | 310 |
| Lysostaphin | 3 | 87 | 74 | 593 |
| Lysostaphin | 4 | 115 | 112 | 83 |
| +Nafcillin (50) | 1 | 7 | 3 | 1125 |
| +Nafcillin | 2 | 15 | 1 | 1 |
| +Nafcillin | 3 | 5 | 39 | 1086 |

MRSA = Methicillin-Resistant *S. aureus*

TABLE 6

| MRSA Group | 10 mg/kg+/ Mouse | Naf Liver | t.i.d. Heart | 4 days Catheter |
|---|---|---|---|---|
| Control | 1 | 583 | 81 | TNTC |
| Control | 2 | 0 | 0 | 334 |
| Control | 3 | 67 | TNTC | TNTC |
| Control | 4 | 0 | 0 | 693 |
| Lysostaphin | 1 | 0 | 0 | 0 |
| Lysostaphin | 2 | 263 | 10 | 932 |
| Lysostaphin | 3 | 28 | 0 | 523 |
| Lysostaphin | 4 | 0 | 0 | 0 |
| +Nafcillin (50) | 1 | 18 | 1 | 15 |
| +Nafcillin | 2 | 0 | 9 | 675 |
| +Nafcillin | 3 | 0 | 0 | 0 |
| +Nafcillin | 4 | 0 | 0 | 0 |

TABLE 7

| MRSA Group | Lysostaphin Mouse | Liver | t.i.d. Heart | 4 days Catheter |
|---|---|---|---|---|
| Control | 1 | 0 | 0 | TNTC |
| Control | 2 | 337 | TNTC | TNTC |
| Control | 3 | 0 | 0 | TNTC |
| 10 mg/kg | 4 | 0 | 0 | 0 |
| 10 mg/kg | 1 | 0 | 0 | 115 |
| 10 mg/kg | 2 | 395 | 3 | 558 |
| 20 mg/kg | 3 | 0 | 0 | 0 |
| 20 mg/kg | 4 | 0 | 0 | 0 |
| 20 mg/kg | 1 | 0 | 0 | 13 |
| 40 mg/kg | 2 | 0 | 0 | 0 |
| 40 mg/kg | 3 | 0 | 0 | 0 |
| 40 mg/kg | 4 | 1 | 0 | 1 |

TABLE 8

| MRSA Group | 15 mg/kg+/ Mouse | Naf Liver | t.i.d. Heart | 4 days Catheter |
|---|---|---|---|---|
| Control | 1 | 0 | 0 | 0 |
| Control | 2 | 105 | 11 | TNTC |
| Control | 3 | 1740 | 80 | TNTC |
| Control | 4 | 0 | 0 | 49 |
| Lysostaphin | 1 | 183 | 2 | 1298 |
| Lysostaphin | 2 | 147 | 0 | 64 |
| Lysostaphin | 3 | 0 | 0 | 0 |
| Lysostaphin | 4 | 245 | 6 | 26 |
| +Nafcillin (50) | 1 | 0 | 0 | 0 |
| +Nafcillin | 2 | 1 | 0 | 0 |
| +Nafcillin | 3 | 0 | 0 | 0 |
| +Nafcillin | 4 | 2 | 0 | 0 |

TABLE 9

| MRSA Group | 15 mg/kg+/ Mouse | Naf Liver | t.i.d. Heart | 4 days Catheter |
|---|---|---|---|---|
| Control | 1 | 279 | 149 | TNTC |
| Control | 2 | 1286 | TNTC | TNTC |
| Control | 3 | 1218 | 62 | TNTC |
| Control | 4 | 1718 | 104 | TNTC |
| Lysostaphin | 1 | 250 | 8 | 35 |
| Lysostaphin | 2 | 10 | 0 | 0 |
| Lysostaphin | 3 | 120 | 0 | 58 |
| Lysostaphin | 4 | 215 | 4 | >1200 |
| +Nafcillin (50) | 1 | 2 | 0 | 0 |
| +Nafcillin | 2 | 0 | 0 | 0 |
| +Nafcillin | 3 | 1 | 0 | 0 |
| +Nafcillin | 4 | 0 | 0 | 0 |

TABLE 10

| MRSA Group | Lysostaphin+ Mouse | Liver | Naf Heart | 4 days Catheter |
|---|---|---|---|---|
| Control | 1 | 0 | 5 | 4 |
| Control | 2 | 0 | 0 | 1040 |
| Control | 3 | 802 | 490 | TNTC |
| Control | 4 | 152 | 114 | TNTC |
| 15 mg/kg-b.i.d. | 1 | 0 | 9 | 9 |
| 15 mg/kg-b.i.d. | 2 | 7 | 0 | 53 |
| 15 mg/kg-b.i.d. | 3 | 18 | 2 | 2 |
| 15 mg/kg-b.i.d. | 4 | 16 | 6 | 10 |
| 10 mg/kg-b.i.d. | 1 | 1144 | 58 | 175 |
| 10 mg/kg-b.i.d. | 2 | 0 | 0 | 2 |
| 10 mg/kg-b.i.d. | 3 | 73 | 9 | 15 |
| 10 mg/kg-b.i.d. | 4 | 0 | 0 | 0 |

TABLE 11

| MRSA Group | Lyso+ Mouse | Naf Liver | t.i.d. Heart | 4 days Catheter |
|---|---|---|---|---|
| Control | 1 | 103 | 92 | TNTC |
| Control | 2 | 306 | 394 | TNTC |
| Control | 3 | 0 | 2 | 66 |
| Control | 4 | 187 | 272 | TNTC |
| 40 (1×)-5 mg/kg | 1 | 20 | 10 | 114 |
| 40 (1×)-5 mg/kg | 2 | 0 | 0 | 0 |
| 40 (1×)-5 mg/kg | 3 | 0 | 0 | 0 |
| 40 (1×)-5 mg/kg | 4 | 16 | 9 | 807 |
| 15 (3×)-5 mg/kg | 1 | 0 | 0 | 0 |
| 15 (3×)-5 mg/kg | 2 | 0 | 0 | 570 |
| 15 (3×)-5 mg/kg | 3 | 3 | 0 | 50 |
| 15 (3×)-5 mg/kg | 4 | 32 | 124 | 237 |

Figure 5A:
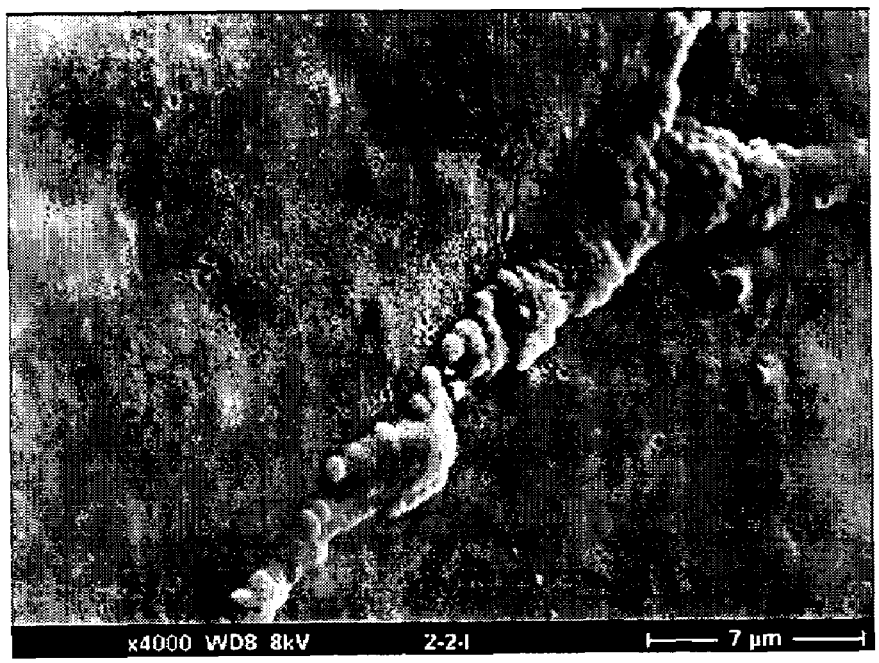
FIGS. 5A and 5B are SEM photographs at 4000× magnification depicting biofilms grown in vivo on a jugular vein catheter from a mouse infected with S. aureus prior to treatment with lysostaphin.
Figure 5B:
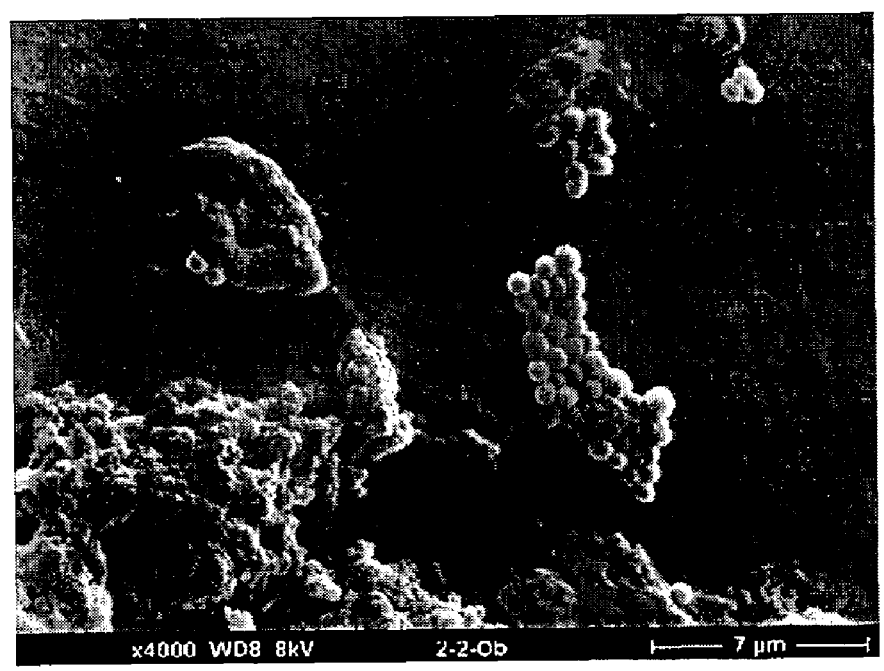
Figure 6A:
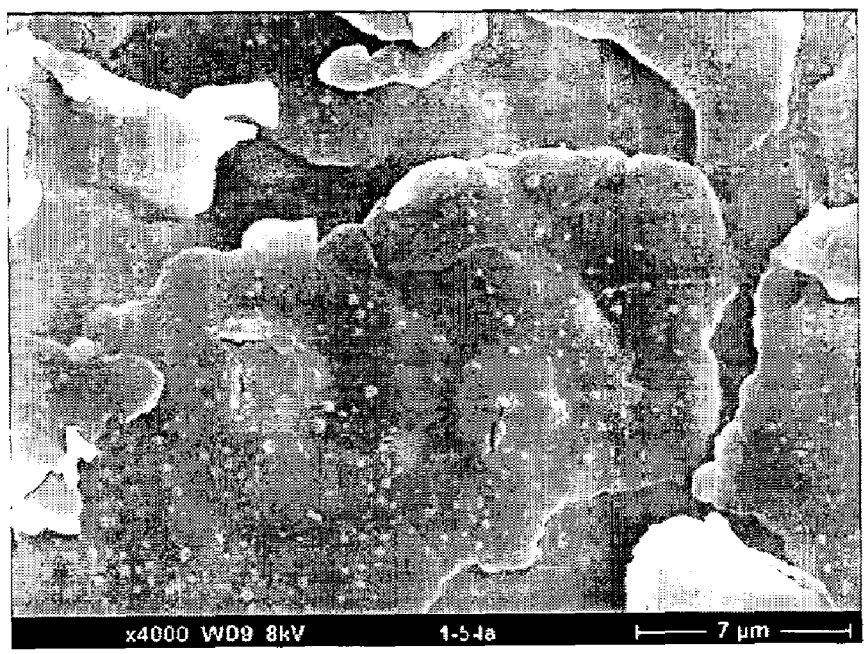
FIGS. 6A and 6B are SEM photographs at 4000×magnification depicting clearance of the biofilms from catheters of S. aureus infected jugular vein catheterized mice (similar to FIG. 5) following treatment with lysostaphin.
Figure 6B:
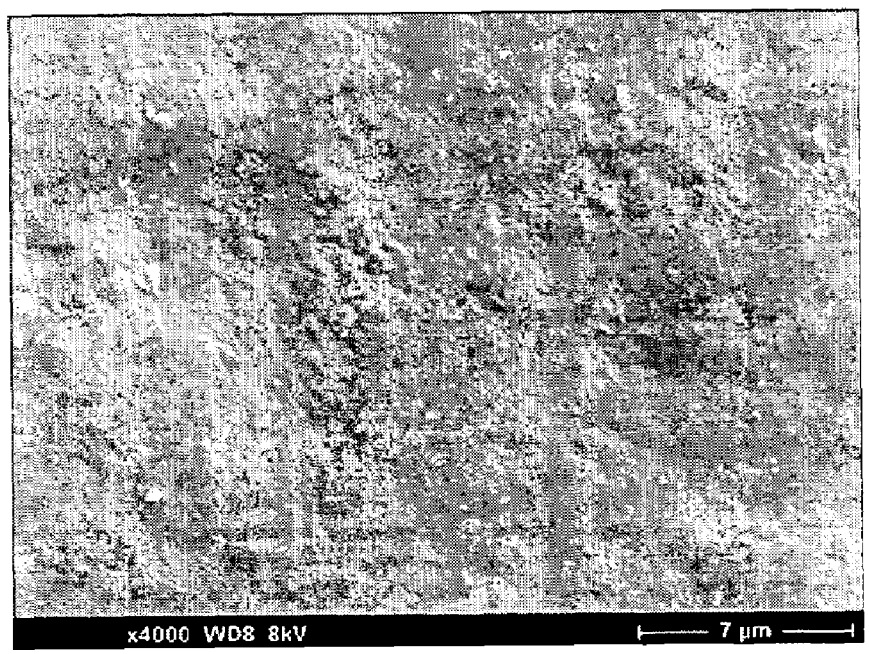

To get clearance of an established catheter infection in mice required 20 mg/kg lysostaphin for methicillin sensitive *S. aureus* and 15 mg/kg+50 mg/kg nafcillin for methicillin-resistant *S. aureus*, t.i.d. for 4 days (Note: lysostaphin and nafcillin are known to have a synergistic killing affect on *S. aureus*). Lower doses of lysostaphin or different dosing regimens (e.g., one dose of 40 mg/kg followed by 5 mg/kg thereafter, or 3 doses of 15 mg/kg the first day followed by 5 mg/kg thereafter) did not result in complete clearance of the *S. aureus* infection. Treating methicillin-resistant *S. aureus* with lysostaphin alone led to the emergence of lysostaphin-resistance in a couple of cases, but combination treatment of methicillin-resistant *S. aureus* with lysostaphin and nafcillin did not result in any lysostaphin-resistance being detected. Lysostaphin-resistance and β-lactam resistance are known to be mutually exclusive. SEM showed that *S. aureus* grew as a biofilm on the implanted catheters (FIG. 5) and that lysostaphin cleared the *S. aureus* biofilm from these catheters (FIG. 6).

Example 7

Pre-Treatment of Catheterized Mice With Lysostaphin

Jugular vein catheterized mice were pretreated with one or two doses of lysostaphin via catheter prior to being challenged with *S. aureus* as in Example 4. The mice received either one dose of lysostaphin (40 mg/kg) 24 hours pre-challenge or two doses of lysostaphin (40 mg/kg) 24 hours and 2 hours pre-challenge. Lysostaphin solutions were left in the catheters during challenge. Control mice received standard Phosphate Buffered Saline (PBS). The mice were sacrificed four days post-challenge.

Two of three control mice had infected catheters, livers and hearts. All eight treated mice were *S. aureus* free.

In the above example, the lysostaphin solution was left in the catheters at the time of bacterial challenge, so it could be argued that this lysostaphin in solution was protecting the catheters from *S. aureus* infection. In order to perform a more rigorous experiment, Catheterized mice were instilled with a single dose of 40 mg/kg lysostaphin in 200 ul PBS through the catheter. One group also received a subsequent 50 ul of lock solution containing the same concentration of lysostaphin as the pre-instillation dose. Twenty two hours later, the catheters of all of these mice were rinsed thoroughly with PBS. Two hours post-rinsing, the animals were challenged with $10^4$ *S. aureus*. The animals were sacrificed 4 days post *S. aureus* challenge and the catheters and organs processed for bacteria. As shown in Table 12, sufficient lysostaphin remained associated with the jugular vein catheters to protect the catheters from *S. aureus* infection, even when excess lysostaphin is rinsed away.

TABLE 12

| Group | Animals infected | CFUs catheter | CFUs heart | CFUs liver |
|---|---|---|---|---|
| Control | 4/4 | >2000 | 880 | 251 |
| Lysostaphin i.c. - no lock | 1/4 | 0 | (287)[a] | (341)[a] |
| Lysostaphin i.c. and lock | 0/4 | 0 | 0 | 0 |

[a]Results from the one infected animal.

The above in vivo examples demonstrate that lysostaphin can clear *S. aureus* biofilms from infected catheters in a mouse model of catheter infection. In these examples a minimum dose of 40 mg/kg administered three times a day for four days was necessary to clear catheters in mice. The above examples further demonstrate that a single dose of 40 mg/kg lysostaphin pre-instilled in catheters in mice will protect the catheters from formation of S. aureus biofilms even when excess lysostaphin is rinsed out of the catheters. These examples are not meant to limit the claims of this patent as doses of lysostaphin necessary to clear or protect mice from biofilm infections may be different than those needed to treat humans and other animals.

The results correlate with the results of Example 3 depicting lysostaphin binding to catheters and maintaining its staphylocidal activity and suggest that the pretreatment of catheters may be more practical than using lysostaphin as a therapy for catheter infections.

Example 8

In Vitro Efficacy of Lysostaphin Coated Intravenous Catheters Materials and Methods Materials. Polystyrene 24 well tissue culture plates were purchased from Costar (Acton, Mass.). The Angiocath catheters and Tryptic Soy Broth were purchased from Becton Dickinson (Sparks, Md.). Phosphate buffered saline, pH 7.2, was purchased from Gibco Life Technologies (Rockville, Md.). Blood agar plates were purchased from Remel (Lenexa, Kans.). Lysostaphin (Ambicin L) was obtained from AMBI, Inc. Bacterial Strains *Staphylococcus aureus* capsule type 5 (SA5) and 8 (clinical isolates); Methicillin-resistant *Staphylococcus aureus* MBT5040 (clinical isolate from WRAMC), *Staphylococcus epidermidis* SE 380 (clinical isolate), 1175 (clinical isolate), ATCC 35984 (purchased from ATCC) were used in the various assays.

Coating of polystyrene wells. Wells were coated with 300 µl of 10 mg/ml, 1 mg/ml or 0.1 mg/ml of lysostaphin diluted in PBS. The plate was incubated overnight at 4° C. Wells were washed with 1 ml of PBS ten times, and washes were removed by vacuum suction. 300 µl of a $5 \times 10^4$ CFU/ml solution of *S. aureus* was added to each well. The plate was shaken at 75 rpm for two hours at 37° C. 40 µl from each well was then removed and streaked onto a blood agar plate and incubated overnight at 37° C.

Coating of Catheters. The needles from the AngioCath catheters were removed and disposed. Using a 1 ml syringe, the catheters were coated with 200 µl of a 0.1 mg/ml solution of lysostaphin. The catheters were incubated for 1 hour, unless otherwise specified, at room temperature. The catheters were then washed with 50 ml of phosphate buffered saline using a peristaltic pump with a flow rate of 1.5 ml/minute. The catheters were then inoculated with 120 µl of a ~$5 \times 10^4$ CFU/ml solution of bacteria (diluted in TSB) and incubated for 2 hours at 37° C. The catheter effluent was then streaked onto a blood agar plate and incubated overnight at 37° C.

Leaching of Lysostaphin. To test whether lysostaphin was slowly being released from the catheter into the lumen solution, lysostaphin coated catheters were incubated with 100 µl PBS for 2 hours at 37° C. The PBS was then transferred into an Eppendorf tube and $10^5$ CFU of SA5 was added to the effluent and incubated for 1 hour at 37° C. 40 µl from the samples were streaked onto blood agar plates and incubated overnight at 37° C. Alternatively, lysostaphin coated catheters were incubated with PBS overnight at 37° C. The following morning the PBS was washed out and the catheters were inoculated with ~$5 \times 10^4$ CFU/ml SA5 for 2 hours at 37° C. The effluent was then streaked onto blood agar plates and incubated at 37° C. overnight. To look for leaching off the polystyrene surface, the wells were coated with 10, 1 and 0.1 mg/ml lysostaphin for 60 minutes. The wells were then washed, and 300 µl of PBS was added to the wells for 2 hours and then removed 300 µl of a $5 \times 10^4$ CFU/ml solution of SA5 was added to the PBS wash and allowed to incubate for one hour at 37° C. 40 µl was then removed and streaked onto a blood agar plate and incubated overnight at 37° C.

Long-term Leaching of Lysostaphin. Ten lysostaphin-coated catheters (10 mg/ml coating concentration) were incubated with PBS for 2 hours at 37° C. The catheters were then washed and two of the ten lysostaphin coated catheters were incubated with 200 µl of a $5 \times 10^4$ CFU/ml solution of SA5 for 2 hours at 37° C. The effluent was streaked on to blood agar plates and incubated at 37° C. overnight. The rest of the catheters were incubated with fresh PBS and left at 37° C. overnight. The following day, all eight catheters were washed out and two of the catheters were incubated with bacteria as above. The other six catheters were again incubated with fresh PBS and left at 37° C. overnight. This procedure was repeated everyday for four days.

Adherence of Bacteria to Catheters. Lysostaphin coated catheters were placed in 2 ml of a 0.1 mg/ml solution of lysostaphin for 2 hours with shaking at 37° C. to coat the outside of the catheter. They were then washed and placed in a $5 \times 10^4$ CFU/ml solution of SA5 and incubated for 3 hours at 37° C. 40 µl of the bacterial solution was streaked on to blood agar plates and incubated at 37° C. overnight. The catheters were incubated in 2 ml TSB overnight at 37° C. and examined for growth. Untreated catheters were washed with 50 ml PBS and then inoculated with 120 µl of a $5 \times 10^6$ CFU/ml solution of bacteria and incubated for 2 or 24 hours. The catheter effluent was then streaked onto blood agar plates and placed at 37° C. overnight. The catheters were washed with 50 ml PBS and the last ml of wash was collected, and 100 µl was streaked onto blood agar plates and incubated at 37° C. overnight. The catheters were then incubated in 1 ml TSB at 37° C. overnight and observed for growth.

Lysostaphin activity in presence of serum proteins. Catheters were coated with 0.1 mg/ml for 60 minutes at room temperature. Catheters were then washed and incubated with human serum or TSB for 24 hours at 37° C. Catheters were washed and then inoculated with $5 \times 10^4$ CFU/ml bacteria for 2 hours at 37° C. The effluent from the catheter was streaked on to blood agar plates and incubated at 37° C. overnight.

The immobilized lysostaphin was able to effectively clear the bacteria from the polystyrene and catheter surfaces. On average, 610 CFU's were recovered from the control wells whereas only 3 CFU's remained in the lysostaphin coated wells, a 99.5% reduction in bacterial counts. The killing was not concentration dependent in these ranges, as all three concentrations were extremely active against the bacteria. The lysostaphin-coated catheters were completely cleared of bacteria as compared to control catheters from which 493 CFU's were recovered. These results suggest that lysostaphin binds to plastic surfaces while still maintaining activity against *S. aureus*.

Figure 10:
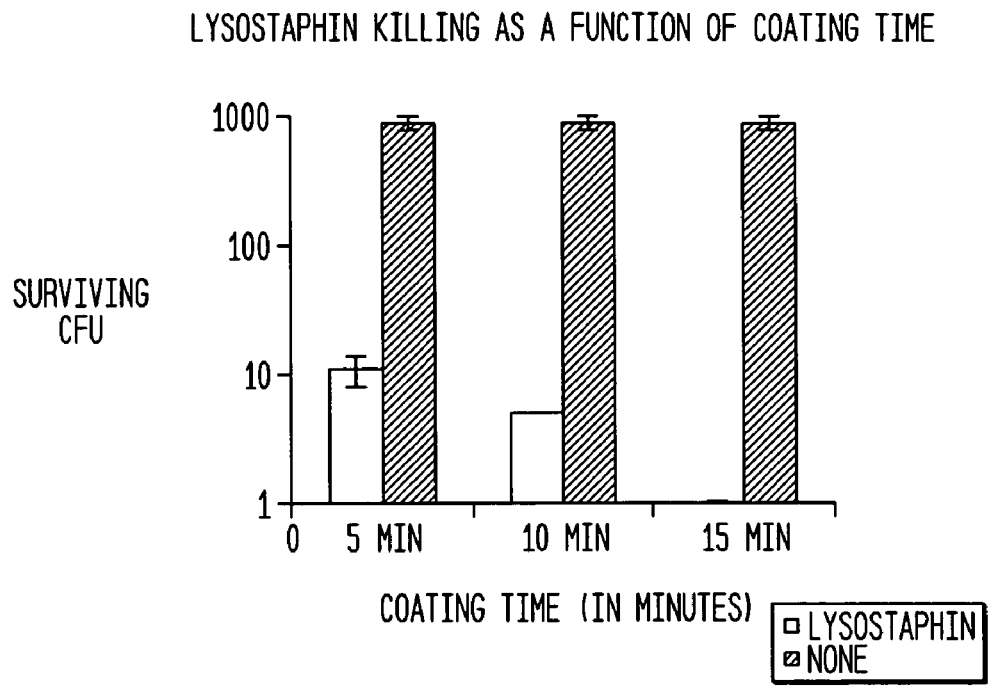
FIG. 10 depicts the antimicrobial efficacy of catheters as a function of lysostaphin coating time.

To determine whether the killing activity was a function of the lysostaphin coating time catheters were coated for 5, 10, or 15 minutes with 0.1 mg/ml lysostaphin and examined for their *S. aureus* killing potency. As shown in FIG. 10, catheters had high levels of killing activity even after just 5 minutes of coating with lysostaphin, but there was a trend for increased efficacy as the coating time was lengthened. Bacterial counts were reduced by 98.7% after coating for 5 minutes, 99.4% after 10 minutes, and completely cleared after just 15 minutes of coating.

Leaching of Lysostaphin Off Coated Surfaces

The PBS wash from the lysostaphin-coated catheters showed only minimal reduction in bacterial counts (Table 14). Lysostaphin coated catheters showed complete clearing of bacteria even after an overnight wash with PBS as opposed to the untreated catheters, from which 1500 CFU's were recovered. This data suggests that if lysostaphin is leaching off the catheter it is doing so in amounts that are not effective against this bacterial challenge.

There is a coating-concentration dependent effect on the clearance of the bacteria as a result of lysostaphin leaching off of polystyrene. The 10 mg/ml wash reduced SA5 titers by 1.4 log reduction compared to control, and with the 1 mg/ml wash there was a 1.3 log reduction. However, at 0.1 mg/ml coating there was only a 0.33 log reduction in bacterial counts due to leaching. In contrast, addition of the same bacterial titer directly to the 0.1 mg/mL coated wells resulted in a 2.4 log reduction in bacterial counts (Table 13).

TABLE 13

Efficacy of surface bound lysostaphin against *S. aureus*.

| Surface | Coating Concentration | CFU (n = 2) |
|---|---|---|
| Polystyrene | 10 mg/ml | 1 |
|  | 1 mg/ml | 1 |
|  | 0.1 mg/ml | 3 |
|  | 0 mg/ml | 610 |
| AngioCath | 0.1 mg/ml | 0 |
|  | 0 mg/ml | 493 |

TABLE 14

Stability of bound lysostaphin and the affect of leaching on antimicrobial efficacy.

| Surface | Coating Concentration | Saline Incubation Time | CFU (n = 3) | Killing In: |
|---|---|---|---|---|
| Angiocath | 0.1 mg/ml | 2 hr | 219 | Wash[1] |
|  | 0 mg/ml | 2 hr | 323 | Wash |
|  | 0.1 mg/ml | 24 hr | 0 | Catheter[2] |
|  | 0 mg/ml | 24 hr | 1503 | Catheter |
| Polystyrene | 10 mg/ml | 2 hr | 26 | Wash |
|  | 1 mg/ml | 2 hr | 33 | Wash |
|  | 0.1 mg/m | 2 hr | 291 | Wash |
|  | 0 mg/ml | 2 hr | 627 | Wash |

[1]Bacteria added to PBS wash
[2]Bacteria added to catheter

Figure 11:
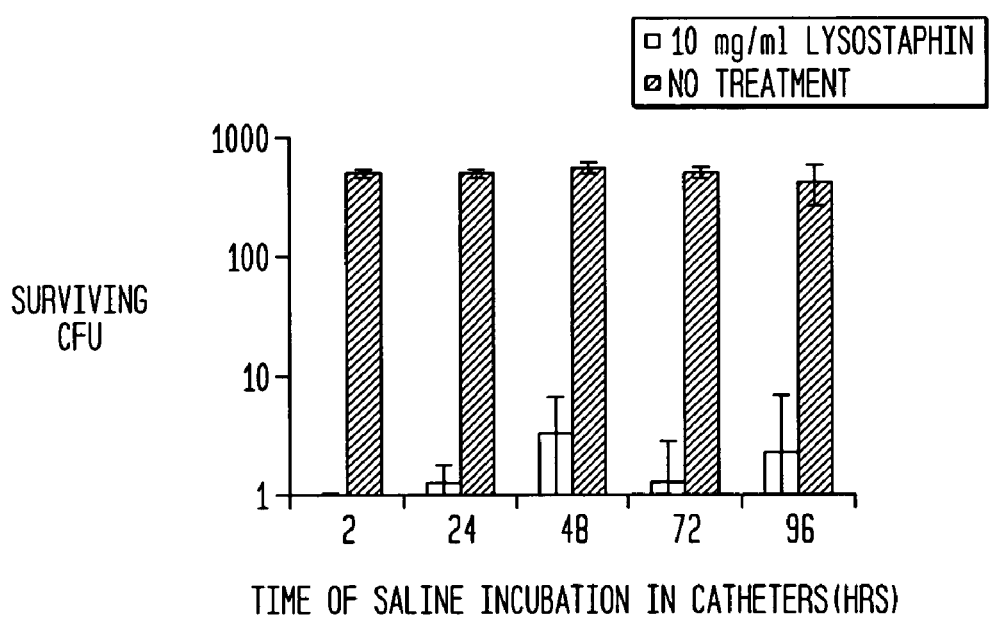
FIG. 11 depicts the long-term antimicrobial effectiveness of lysostaphin-coated catheters against S. aureus.

The effect of continuous leaching of lysostaphin on the killing activity of coated catheters is shown in FIG. 11. Catheters were incubated with PBS for up to 96 hours, with PBS being refreshed every 24 hours. The catheters were then challenged with bacteria to determine if they maintained their *S. aureus* killing activity. As shown in FIG. 11, after a two-hour incubation with PBS, there was a 2.8 log reduction in the bacteria recovered from the lysostaphin-coated catheters as compared to the uncoated catheters. At 24 hours there was a 1.8 log reduction in bacterial counts, a 1.5 log reduction at 48 hours, a 0.7 log reduction at 72 hours, and after 96 hours there was a 0.3 log reduction in bacterial counts.

Susceptibility of Various Strains to Lysostaphin Coated Catheters

Table 15 depicts the susceptibility of several *S. aureus* and *S. epidermidis* strains tested in the in vitro catheter model, including an MRSA strain and an archetypical biofilm producing *S. epidermidis* strain.

TABLE 15

Susceptibility of various Staphylococcal strains to lysostaphin coated catheters.

| Coating Concentration | Bacteria Strain | CFU (n = 2) |
|---|---|---|
| 0.1 mg/ml | *S. epi* 380 | 4 |
| 0 mg/ml | *S. epi* 380 | 678 |
| 0.1 mg/ml | *S. epi* 1175 | 68 |
| 0 mg/ml | *S. epi* 1175 | 824 |
| 0.1 mg/ml | *S. epi* 35984 | 16 |
| 0 mg/ml | *S. epi* 35984 | 757 |
| 0.1 mg/ml | SA5 | 1 |
| 0 mg/ml | SA5 | 785 |
| 0.1 mg/ml | SA8 | 0 |
| 0 mg/ml | SA8 | 1593 |
| 0.1 mg/ml | MRSA | 1 |
| 0 mg/ml | MRSA | 910 |

Previous studies have shown lysostaphin to be less active against *S. epidermidis* as compared to *S. aureus*, however the lysostaphin-coated catheters were able to effectively kill three strains of *S. epidermidis*, though slightly less efficiently than the *S. aureus* strains. *S. epidermidis* type 380 was the most susceptible of the *S. epidermidis* strains with a 2.2 log reduction. Biofilm producing *S. epidermidis* ATCC 35984 had a 1.8 log reduction, and *S. epidermidis* 1175 showed a 1.1 log reduction from the control sample. The lysostaphin-coated catheters were very active against both *S. aureus* MBT5040 (MRSA) and *S. aureus* capsule type 8 (SA8). On average, 1 CFU was recovered from the catheters incubated with MRSA, whereas catheters incubated with SA8 were completely cleared, as compared to 1250 CFU's recovered from the uncoated catheters.

Adherence of Bacteria to Catheter

The number of bacteria in the uncoated catheter effluent were too numerous to count, however, the last ml of the wash was collected and streaked onto a blood agar plate. The amount of bacteria in the wash was proportional to the incubation time, with more bacteria adhering at twenty fours. On average, 1000 CFU's were recovered from the 24-hour washes, whereas about 30 CFU's were recovered from the 2-hour washes. The number of bacteria in the wash is likely to be indicative of the level of adherence of the bacteria in the catheter. The uncoated catheters were then cultured and examined for bacterial growth. An overnight incubation in media showed that the catheters were well colonized and the bacteria grew in the media. This data suggests that bacteria do adhere to the surface of the catheter and could cause infection. The lysostaphin catheters that were incubated in a high inoculum of bacteria for 3 hrs, cleared the solution. Following an overnight incubation, the media was clear, suggesting that the lysostaphin-coated catheters were able to clear the bacterial solution in 3 hours, and the catheters remained sterile.

Lysostaphin Activity in Presence of Serum Proteins

Figure 12:
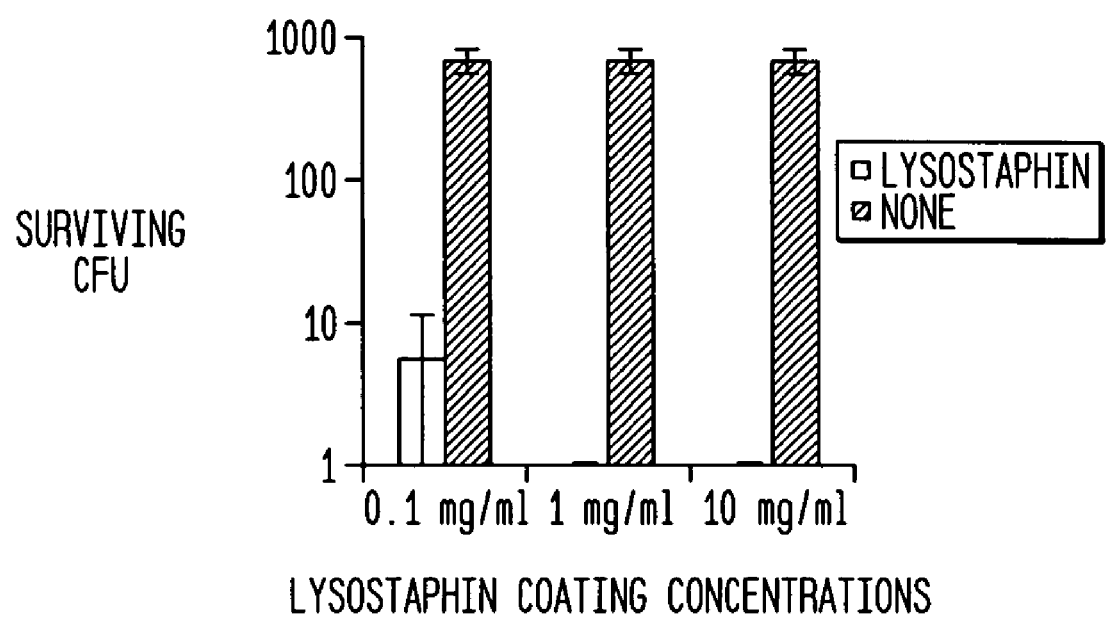
FIG. 12 depicts the antimicrobial efficacy of lysostaphin-coated catheters in the presence of serum proteins.

As shown in FIG. 12, the 0.1 mg/ml lysostaphin coated catheters incubated with human serum showed a 99% reduction in bacterial counts, whereas the 10 and 1 mg/ml lysostaphin coated catheters incubated with human serum completely cleared the bacteria. These results suggest that the presence of serum proteins do not significantly affect the activity of lysostaphin on the catheters.

The foregoing examples demonstrate the efficacy of coating lysostaphin onto artificial surfaces. Lysostaphin coated surfaces may become an important new therapy in the prevention of both catheter and implant related infections.

As will be readily appreciated, numerous variations and combinations of the features set forth above can be utilized without departing from the invention as set forth in the claims. The variations are not regarded as a departure from the spirit and scope of the invention, and all such modifications are intended to be included within the scope of the following claims.

What is claimed is:

1. A method for treating a patient possessing an indwelling prosthetic device or catheter, wherein said indwelling prosthetic device or catheter is in contact with a biofilm, comprising administering to said patient lysostaphin under conditions such that said biofilm is disrupted.
2. The method of claim 1, wherein disrupting said biofilm comprises eradicating said biofilm.
3. The method of claim 1, wherein altering said bioflim comprises killing bacteria involved in forming said biofilm.
4. The method of claim 3, wherein said bacteria comprise S. aureus.
5. The method of claim 3, wherein said bacteria comprise S. epidermidis.
6. The method of claim 1, wherein said lysostaphin is co-administered with one or more antibacterial agents.
7. The method of claim 6, wherein said antibacterial agents are selected from the group consisting of antibiotics, antibodies, antibacterial enzymes, peptides, lantibiotics, and lanthione-containing molecules.
8. The method of claim 1, wherein said lysostaphin is co-administered with an antibiotic effective against staphylococci.
9. The method of claim 8, wherein said antibiotic interferes with or inhibits cell wall synthesis.
10. The method of claim 9, wherein said antibiotic is selected from the group consisting of β-lactams, cephalosporins, glycopeptides, aminoglycosides, sulfonomides, macrolides, folates, polypeptides and combinations thereof.
11. The method of claim 8, wherein said antibiotic interferes with protein synthesis.
12. The method of claim 11, wherein said antibiotic is selected from the group consisting of glycosides, tetracyclines and streptogramins.
13. The method of claim 1, wherein said biofilm comprises bacteria from the genus Staphylococcus.
14. The method of claim 1, wherein said biofilm comprises S. aureus.
15. The method of claim 1, wherein said biofilm comprises S. epidermidis.
16. The method of claim 1, wherein said biofilm comprises S. aureus and S. epidermidis.
17. The method of claim 14, wherein said S. aureus is antibiotic resistant.
18. The method of claim 14, wherein said S. aureus is methicillin resistant.
19. The method of claim 14, wherein said S. aureus is vancomycin resitant.
20. The method of claim 15, wherein said S. epidermidis is antibiotic resistant.
21. The method of claim 15, wherein said S. epidermidis is methicillin resitant.
22. The method of claim 15, wherein said S. epidermidis is vancomycin resitant.
23. The method of claim 1, wherein said lysostaphin is recombinant lysostaphin having the same enzymatic activity as lysostaphin.
24. The method of claim 23, wherein said recombinant lysostaphin is full length lysostaphin or a fragment thereof having the same enzymatic activity of lysostaphin wherein said enzymatic activity comprises cleaving cross-linked polyglycine bridges.
25. The method of claim 1, wherein said lysostaphin is synthetically constructed.
26. The method of claim 1, wherein said lysostaphin is administered to said patient in a single dose.
27. The method of claim 1, wherein said lysostaphin is administered to said patient in multiple doses.
28. The method of claim 27, wherein said multiple doses are administered on separate days.
29. The method of claim 27, wherein said multiple doses are administered on the same day.
30. The method of claim 1, wherein said lysostaphin is administered continuously.
31. The method of claim 1, wherein said lysostaphin is administered to said patient so as to provide between 1 and 50 milligrams of lysostaphin per kilogram of patient bodyweight per day.
32. The method of claim 1, wherein said lysostaphin is administered to said patient so as to provide between 25 and 50 milligrams of lysostaphin per kilogram of patient bodyweight per day.
33. The method of claim 6, wherein co-administration with lysostaphin permits administering a lower dose of said antibacterial agent than would be administered without co-administration of lysostaphin.
34. The method of claim 8, wherein co-administration with lysostaphin permits administering a lower dose of said antibiotic than would be administered without co-administration of lysostaphin.
35. The method of claim 1, wherein said lysostaphin is administered intravenously.
36. The method of claim 1, wherein said lysostaphin is administered directly into an infected site.
37. The method of claim 1, wherein said lysostaphin is administered directly onto said indwelling prosthetic device or catheter.
38. The method of claim 1, wherein said indwelling device is a shunt.
39. The method of claim 1, wherein said indwelling device is a stent.
40. The method of claim 1, wherein said indwelling device is a scaffold for tissue construction.
41. The method of claim 1, wherein said indwelling device is a gastric feeding tube.
42. The method of claim 1, wherein said indwelling device is a punctual plug.
43. The method of claim 1, wherein said indwelling device is an artificial joint.
44. The method of claim 1, wherein said indwelling device is a pacemaker.
45. The method of claim 1, wherein said indwelling device is an artificial valve.

46. The method of claim 1, wherein said lysostaphin treats an infection associated with damaged tissue associated with said indwelling device or catheter.

47. The method of claim 1, wherein said lysostaphin is administered directly through said catheter.

48. The method of claim 26, wherein said single dose delivers to said patient about 100 milligrams of lysostaphin per kilogram bodyweight of said patient.

49. The method of claim 1, wherein said lysostaphin is administered to said patient so as to provide greater than 60 milligrams of lysostaphin per kilogram of patient bodyweight.

50. The method of claim 20, wherein said lysostaphin is administered in multiple doses.

* * * * *

UNITED STATES PATENT AND TRADEMARK OFFICE
CERTIFICATE OF CORRECTION

PATENT NO. : 7,572,439 B2 Page 1 of 1
APPLICATION NO. : 10/401342
DATED : August 11, 2009
INVENTOR(S) : Kokai-Kun et al.

It is certified that error appears in the above-identified patent and that said Letters Patent is hereby corrected as shown below:

The Cross-Reference to Related Application section beginning in column 1, line 7, reads:

"The present application claims priority benefit under 35 U.S.C. §119(e) of U.S. Provisional Application Serial No. 60/367,189 filed on Mar. 26, 2002, the disclosure of which is incorporated herein by reference."

when in fact it should read:

--The present application claims priority benefit under 35 U.S.C. §119(e) of U.S. Provisional Application Serial No. 60/367,819 filed on Mar. 26, 2002, the disclosure of which is incorporated herein by reference.--

Signed and Sealed this

Twenty-ninth Day of June, 2010

David J. Kappos
*Director of the United States Patent and Trademark Office*